United States Patent
Planelles et al.

(10) Patent No.: US 11,066,651 B2
(45) Date of Patent: Jul. 20, 2021

(54) METHODS AND COMPOSITIONS RELATING TO VIRAL LATENCY

(71) Applicant: University of Utah Research Foundation, Salt Lake City, UT (US)

(72) Inventors: Vicente Planelles, Salt Lake City, UT (US); Alberto Bosque, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 151 days.

(21) Appl. No.: 16/522,371

(22) Filed: Jul. 25, 2019

(65) Prior Publication Data

US 2020/0087631 A1   Mar. 19, 2020

Related U.S. Application Data

(63) Continuation of application No. 15/645,505, filed on Jul. 10, 2017, now abandoned, which is a continuation of application No. 12/695,075, filed on Jan. 27, 2010, now Pat. No. 9,719,069.

(60) Provisional application No. 61/147,649, filed on Jan. 27, 2009.

(51) Int. Cl.
   *C12N 7/00* (2006.01)

(52) U.S. Cl.
   CPC ...... *C12N 7/00* (2013.01); *C12N 2740/16052* (2013.01)

(58) Field of Classification Search
   CPC .... A61K 49/00; A61K 49/0097; A61K 39/21; A61K 2035/124; C12N 2740/16063; C12N 15/86; C12N 15/907; C12N 2510/00; C12N 5/16; C12N 15/79; C12N 15/85; C12N 2501/515; C12N 2840/007; C12N 5/0638; C12N 15/1132; C12N 15/1138; C12N 2740/10051; C12N 2740/15045; C12N 2740/16271; C12N 2740/16334; C12N 2760/16134
   See application file for complete search history.

(56) References Cited

U.S. PATENT DOCUMENTS

| | | |
|---|---|---|
| 6,790,657 B1 | 9/2004 | Arya |
| 6,962,810 B2 | 11/2005 | Fraser et al. |
| 7,226,780 B2 | 6/2007 | Arya |
| 9,730,928 B2 | 8/2017 | Planelles et al. |
| 2010/0291067 A1 | 11/2010 | Planelles et al. |
| 2011/0305774 A1 | 12/2011 | Savarino et al. |
| 2017/0360784 A1 | 12/2017 | Planelles et al. |

FOREIGN PATENT DOCUMENTS

| | | |
|---|---|---|
| EP | 3008043 A2 | 4/2016 |
| WO | WO-1993/025234 A1 | 12/1993 |
| WO | WO-1994/006920 A1 | 3/1994 |
| WO | WO-2014/201426 A2 | 12/2014 |

OTHER PUBLICATIONS

Pierson T, et al. Identification of a reservoir for HIV-1 in patients on highly active antiretroviral therapy. Science. 1997; 278: 1295-1300.*
Folks TM. et al. Tumor necrosis factor alpha induces expression of human immunodeficiency virus in a chronically infected T-cell clone. Proc Natl Acad Sci U S A. 1989; 86:2365-2368.*
Abraham, R.T. et al. (2004) Jurkat T cells and development of the T-cell receptor signalling paradigm. Nat Rev Immunol. 4(4):301-8.
Akkina, R.K. et al. (1996) High-efficiency gene transfer into CD34+ cells with a human immunodeficiency virus type 1-based retroviral vector pseudotyped with vesicular stomatitis virus envelope glycoprotein G. J Virol. 70(4):2581-5.
Andersen, J.L. et al. (2006) HIV-1 Vpr-induced apoptosis is cell cycle dependent and requires Bax but not ANT. PLoS Pathog. 2(12):e127.
Andrea (2012) Basic markers of T cell populations in human PBMC, PBMC Basic. pp. 1-2.
Antoni, B.A. et al. (1994) NF-κ B-dependent and -independent pathways of HIV activation in a chronically infected T cell line. Virology. 202(2):684-94.
Archin et al. (2009) Expression of latent human immunodeficiency type 1 is induced by novel and selective histone deacetylase inhibitors. AIDS. 23(14):1-16.
Bauer, B. et al. (2000) T cell expressed PKCtheta demonstrates cell-type selective function. Eur J Immunol, 30(12):3645-54.
Bosque, A. et al (2009) Induction of HIV-1 latency and reactivation in primary memory CD4+ T cells. Blood. 113:58-65.
Bosque, A. et al (2010) Studies of HIV-1 latency in an ex vivo model that uses primary central memory T cells. Methods, 53(1):54-61 (17 pages).
Bosque, A. et al (2011) Homeostatic Proliferation Fails to Efficiently Reactivate HIV-1 Latently Infected Central Memory CD4+ T Cells. PLOS Pathog. 7(10):e1002288 (8 pages).
Brenchley et al. (2002) Expansion of activated human naïve T-cells precedes effector Function, Clin Exp Immunol. 130(3):431-40.
Brenchley, J.M. et al. (2004) T-cell subsets that harbor human immunodeficiency virus (HIV) in vivo: implications for HIV pathogenesis. J Virol. 78(3):1160-8.
Brooks, D.G. et al. (2001) Generation of HIV latency during thymopoiesis. Nat Med. 7(4):459-64.
Brooks, D.G. et al. (2003) Molecular characterization, reactivation, and depletion of latent HIV. Immunity. 19(3):413-23.
Butera, S.T. et al. (1994) Human immunodeficiency virus type 1 RNA expression by four chronically infected cell lines indicates multiple mechanisms of latency. J Virol. 68(4):2726-30.
Butler, S.L. et al. (2001) A quantitative assay for HIV DNA integration in vivo. Nat Med. 7(5):631-4.
Böhnlein, E. et al. (1988) The same inducible nuclear proteins regulate mitogen activation of both the interleukin-2 receptor-alpha gene and type 1 HIV. Cell. 53(5):82736.

(Continued)

*Primary Examiner* — Bao Q Li
(74) *Attorney, Agent, or Firm* — Ballard Spahr LLP

(57) ABSTRACT

Disclosed are compositions and methods that relate generally to viruses, and more particularly to the agents and their identification and use of anti-HIV agents which cause latently infected cells to reactivate.

15 Claims, 16 Drawing Sheets

Specification includes a Sequence Listing.

(56) References Cited

OTHER PUBLICATIONS

Cannon, P. et al. (1994) Analysis of Tat function in human immunodeficiency virus type 1-infected low-level-expression cell lines U1 and ACH-2. J Virol. 68(3):1993-7.
Caux et al. (1997) CD34+ Hematopoetic Progenitors From Human Cord Blood Differentiate Along Two Independent Dendritic Cell Pathways in Response to Granulocyte-Macrophage Colony-Simulating Factor Plus Tumor Necrosis Facor, Blood. 90(4):1458-70.
Challita-Eid, P.M. et al. (1998) Inhibition of HIV type 1 infection with a RANTES-IgG3 fusion protein. AIDS Res Hum Retroviruses. 14(18)1617-24.
Chen, B.K. et al. (1994) Distinct modes of human immunodeficiency virus type 1 proviral latency revealed by superinfection of nonproductively infected cell lines with recombinant luciferase-encoding viruses. J Virol. 68(2):654-60.
Chun, T.W. et al (1997) Quantification of latent tissue reservoirs and total body viral load in HIV-1 infection. Nature. 387:183-8.
Costello et al. (2000) Gene Transfer to simulated and unstimulated T Lymphocytes by HIV-1 derived lentiviral vectors, Gene Therapy. 7(7):596-604.
Cruse et al. (2003) Illustrated Dictionary of Immunology, second edition, CRC PRESS, pp. 160 and 345.
D'Adda di Fagagna, F. et al. (1995) Molecular and functional interactions of transcription factor USF with the long terminal repeat of human immunodeficiency virus type 1. J Virol. 69(5):2765-75.
Dardalhon et al. (2000) Highly efficient gene transfer in native human T cells with a murine leukemia virus-based vector. Gene Ther. 96(3):885-93.
Davis et al. (2004) ABC transporter inhibitors that are substrates enhance lentiviral vector transduction into primative hematopoietic progenitor cells, Blood. 104 (2): 363-73.
DeHart, J.L. et al. (2005) The ataxia telangiectasia-mutated and Rad3-related protein is dispensable for retroviral integration. J Virol. 79(3):1389-96.
Dienz, O. et al. (2007) Accumulation of NFAT mediates IL-2 expression in memory, but not naïve, CD4+ T cells. Proc Natl Acad Sci U S A. 104(17):7175-80.
Douek, D.C. et al. (2003) T cell dynamics in HIV-1 infection. Annu Rev Immunol. 21:265-304.
Douglas, J.L. et al. (2001) Efficient human immunodeficiency virus-based vector transduction of unstimulated human mobilized peripheral blood CD34+ cells in the SCID-hu Thy/Liv model of human T cell lymphopoiesis. Hum Gene Ther. 12(4):401-13.
Duh, E.J. et al. (1989) Tumor necrosis factor alpha activates human immunodeficiency virus type 1 through induction of nuclear factor binding to the NF-kappa B sites in the long terminal repeat. Proc Natl Acad Sci U S A. 86(15):5974-8.
Etienne-Julan, M. et al. (1992) The efficiency of cell targeting by recombinant retroviruses depends on the nature of the receptor and the composition of the artificial cell-virus linker. J Gen Virol. 73 (Pt 12):3251-5.
Finzi, D. et al. (1997) Identification of a reservoir forHIV-1 in patients on highly active antiretroviral therapy. Science. 278:1295-1300.
Folks, T.M. et al. (1987) Cytokineinduced expression of HIV-1 in a chronically infected promonocyte cell line. Science. 238: 800-2.
Folks, T.M. et al. (1989) Tumor necrosis factor alpha induces expression of human immunodeficiency virus in a chronically infected T-cell clone. Proc Natl Acad Sci U S A. 86(7):2365-8.
Franke, T.F. et al. (1995) The protein kinase encoded by the Akt proto-oncogene is a target of the PDGF-activated phosphatidylinositol 3-kinase. Cell. 81(5):727-36.
Fu et al. (2010) Discovery of 1 H-benzo[d][1,2,3] triazol-1-yl 3,4,5-trimethoxybenzoate as a potential antiproliferative agent inhibiting histone deacetylase. Bioorg Med Chem. 18: 8457-62.
Giffin, M.J. et al. (2003) Structure of NFAT1 bound as a dimer to the HIV-1 LTR kappa B element. Nat Struct Biol. 10(10):800-6.

Goud, B. et al. (1988) Antibody-mediated binding of a murine ecotropic Moloney retroviral vector to human cells allows internalization but not the establishment of the proviral state. Virology. 163(1):251-4.
Gómez-Benito, M. et al. (2005) Apo2L/TRAIL is an indirect mediator of apoptosis induced by interferon-alpha in human myeloma cells. FEBS Lett. 579(27):6217-22.
Hintzen, R.Q. et al. (1993) Regulation of CD27 Expression on Subset of Mature T-Lymphocytes. J Immunol. 151(5): 2426-35.
Hörig, H. et al., From Bench to Clinic and Back: Perspective on the 1st IQPC Translational Research Conference. J Transl Med. 2004; 2:44 (8 pages).
Humearu et al. (2004) Efficient Lentiviral Vector-Mediated Control of HIV-1 Replication in CD4 Lymphocytes from Diverse HIV+ Infected Patients Grouped According to CD4 Count and Virl Load. Mol Ther. 9:902-13.
Isakov, N. et al. (1987) T-lymphocyte activation: the role of protein kinase C and the bifurcating inositol phospholipid signal transduction pathway. Immunol Rev. 95:89-111.
Jones, K.A. et al. (1986) Activation of the AIDS retrovirus promoter by the cellular transcription factor, Sp1. Science. 232(4751):755-9.
Jordan, A. et al. (2003) HIV reproducibly establishes a latent infection after acute infection of T cells in vitro. Embo J 22:1868-1877.
Kane, L.P. et al. (2000) Signal transduction by the TCR for antigen. Curr Opin Immunol, 12(3):242-9.
Kim, Y.K. et al. (2006) Recruitment of TFIIH to the HIV LTR is a rate-limiting step in the emergence of HIV from latency. EMBO J. 25(15):3596-604.
Lacroix, I. et al. (2002) Sp1 transcriptional activity is up-regulated by phosphatase 2A in dividing T lymphocytes. J Biol Chem. 277(11):9598-605.
Lahm, H.W. et al. (1985) Characterization of recombinant human interleukin-2 with micromethods. J Chromatogr. 326:357-61.
Lehrman, G. et al. (2005) Depletion of latent HIV-1 infection in vivo: a proof-of-concept study. Lancet. 366(9485):549-55.
Lin, J. et al. (2001) T cell receptor signaling. J Cell Sci. 114(Pt 2):243-4.
Lu et al. (2004) Safe two-plasmid production for the first clinical lentivirus vector that achieves > 99% transduction in primary cells using a one-step protocol. J Gene Med. 6: 963-73.
Luther-Wyrsch, A. et al. (2001) Stable transduction with lentiviral vectors and amplification of immature hematopoietic progenitors from cord blood of preterm human fetuses. Hum Gene Ther. 12(4):377-89.
Messi, M. et al. (2003) Memory and flexibility of cytokine gene expression as separable properties of human T(H)1 and T(H)2 lymphocytes. Nat Immunol. 4(1):78-86.
Muhlebach et al. (2005) Stable Transduction of Primary Human Monocytes by Simian Lentiviral Vector PBj. Mol Ther. 12: 1206-16.
Nakamura, I. et al., Transition-Metal-Catalyzed Reactions in Heterocylic Synthesis. Chem Rev. 2004; 104: 2127-98.
Neda, H. et al. (1991) Chemical modification of an ecotropic murine leukemia virus results in redirection of its target cell specificity. J Biol Chem. 266(22):14143-6.
Newcomb et al. (2009) Chapter 9, Umbilical Cord Blood cells in Methods in Molecular Biology. Neura cell Transplantation. 549:119-36.
Nordheim, A. (1994) Transcription factors. CREB takes CBP to tango. Nature. 370(6486):177-8.
Osborn, L. et al. (1989) Tumor necrosis factor alpha and interleukin 1 stimulate the human immunodeficiency virus enhancer by activation of the nuclear factor kappa B. Proc Natl Acad Sci U.S.A. 86(7):2336-40.
Perkins, N.D. et al. (1994) Transcription factor AP-2 regulates human immunodeficiency virus type 1 gene expression. J Virol. 68(10):6820-3.
Persaud, D. et al. (2003) Latency in human immunodeficiency virus type 1 infection: no easy answers. J Virol. 77(3):1659-65.
Poeschla, E. et al. (1996) Development of HIV vectors for anti-HIV gene therapy. Proc Natl Acad Sci U.S.A. 93(21):11395-9.
Qui et al. (2000) Analysis of Surface markers of expanded human umbilical cord blood cells in vitro, 21(8): 409-11 (Abstract only).

(56) References Cited

OTHER PUBLICATIONS

Rivino, L. et al. (2004) Chemokine receptor expression identifies Pre-T helper (Th)1, Pre-Th2, and nonpolarized cells among human CD4+ central memory T cells. J Exp. Med. 200(6):725-35.

Round, J.L. et al. (2007) Scaffold protein Dlgh1 coordinates alternative p38 kinase activation, directing T cell receptor signals toward NFAT but not NF-kappaB transcription factors. Nat Immunol. 8(2):154-61.

Roux, P. et al. (1989) A versatile and potentially general approach to the targeting of specific cell types by retroviruses: application to the infection of human cells by means of major histocompatibility complex class I and class II antigens by mouse ecotropic murine leukemia virus-derived viruses. Proc Natl Acad Sci U S A. 86(23):9079-83.

Ruocco, M.R. et al. (1996) Regulation of HIV-1 long terminal repeats by interaction of C/EBP(NF-IL6) and NF-kappaB/Rel transcription factors. J Biol Chem. 271(37):22479-86.

Schäfer et al., Failure is an Option: Learning from Unsuccessful Proof-of-Concept Trials. Drug Discov Today. 2008; 13(21/22):913-6.

Sheridan PL, et al. (1995) Activation of the HIV-1 enhancer by the LEF-1 HMG protein on nucleosome-assembled DNA in vitro. Genes Dev. 9(17):2090-2104.

Simm M, et al. (1995) Aberrant Gag protein composition of a human immunodeficiency virus type 1 vif mutant produced in primary lymphocytes. J Virol. 69(7):4582-4586.

Simon G, et al. (1994) Valproic acid reduces the intracellular level of glutathione and stimulates human immunodeficiency virus. Chem Biol Interact. 91(2-3):111-121.

Svarovskaia, E.S. et al. (2004) Azido-containing diketo acid derivatives inhibit human immunodeficiency virus type 1 integrase in vivo and influence the frequency of deletions at two-long-terminal-repeat-circle junctions. J Virol. 78(7):3210-22.

Swaroop, N. et al. (2001) Inhibition of nuclear transcription factor-kappaB by specific IkappaB kinase peptide inhibitor, Pharm Res. 18(11):1631-3.

Tesmer, V.M. et al. (1993) NF-IL6-mediated transcriptional activation of the long terminal repeat of the human immunodeficiency virus type 1. Proc Natl Acad Sci U.S.A. 90(15):7298-302.

Vandegraaff, N. et al. (2001) Specific inhibition of human immunodeficiency virus type 1(HIV-1) integration in cell culture: putative inhibitors of HIV-1 integrase. Antimicrob Agents Chemother. 45(9):2510-6.

Vicart, A. et al. (2006) Increased chromatin association of Sp1 in interphase cells by PP2A-mediated dephosphorylations. J Mol Biol. 364(5):897-908.

Ylisastigui, L. et al. (2004) Coaxing HIV-1 from resting CD4 T. cells: histone deacetylase inhibition allows latent viral expression. AIDS. 18(8):1101-8.

Zhu, Y. et al. (2001) Comparison of cell cycle arrest, transactivation, and apoptosis induced by the simian immunodeficiency virus SIVagm and human immunodeficiency virus type 1 vpr genes. J Virol. 75(8):3791-801.

* cited by examiner

SEQUENCE LISTING

```
<160> NUMBER OF SEQ ID NOS: 16

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 1
tgacatcgag cttgctacaa ctcactttcc gctggggac                              39

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 2
gtccccagcg gaaagtgagt tgtagcaagc tcgatgtc                               38

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Note =
      Synthetic Construct
```

<400> SEQUENCE: 3 aagggactttt ccgctgctca ctttccaggg aggcg                                       35

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 4
cgcctccctg gaaagtgagc ggaaagtccc tt                                           32

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 5
cttgctacaa gggactttcc atatgggact ttccagggag gcgt                              44

<210> SEQ ID NO 6
<211> LENGTH: 43
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 6
cgcctccctg gaaagtccca tatggaaagt cccttgtagc aag                               43

<210> SEQ ID NO 7
<211> LENGTH: 49
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 7
ggggactttc cagggattcg tggcctgttc gggactggtt agtggcgag                         49

<210> SEQ ID NO 8
<211> LENGTH: 49
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 8
ctcgccacta accagtcccg aacaggccac gaatccctgg aaagtcccc                         49

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 9
gtttgacagc cgcctagcat ttcatgaatt cgcccgagag ctgc       44

<210> SEQ ID NO 10
<211> LENGTH: 44
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 10
gcagctctcg ggcgaattca tgaaatgcta ggcggctgtc aaac       44

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 11
gctgcatccg gagtacgaat tcaactgctg acatcgagc       39

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 12
gctcgatgtc agcagttgaa ttcgtactcc ggatgcagc       39

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 13
ttgacagccg cctagcattt aatcacgtgg cc       32

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 14
ggccacgtga ttaaatgcta ggcggctgtc aa       32

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 15

```
cttcaagaac tgctgacatc gagagctgta caagggactt tccgctgggg a            51
```

<210> SEQ ID NO 16
<211> LENGTH: 51
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 16

```
tccccagcgg aaagtccctt gtacagctct cgatgtcagc agttcttgaa g            51
```

METHODS AND COMPOSITIONS RELATING TO VIRAL LATENCY

CROSS-REFERENCE TO RELATED APPLICATIONS

This application is a continuation of U.S. application Ser. No. 15/645,505, filed Jul. 10, 2017, which is a continuation of U.S. application Ser. No. 12/695,075, filed Jan. 27, 2010, which claims the benefit of U.S. Provisional Application No. 61/147,649, filed on Jan. 27, 2009, which is incorporated by reference herein in its entirety.

STATEMENT REGARDING FEDERALLY SPONSORED RESEARCH

This invention was made with government support under Grant AI49057 awarded by the National Institutes of Health. The government has certain rights in the invention.

SEQUENCE LISTING

The Sequence Listing submitted herewith as a text file named "21101_0176U4_Sequence_Listing," created on Jul. 25, 2019, and having a size of 4,098 bytes is hereby incorporated by reference pursuant to 37 C.F.R. § 1.52(e)(5).

BACKGROUND

The advent of highly active antiretro viral therapy (HAART), which involves the use of three or more antiretroviral drugs, has led to a significant improvement in the care and survival of patients infected with HIV-I. In patients not infected with resistant strains of the virus, HAART typically results in a dramatic decrease in viral load often from levels of 10,000-100,000 RNA copies/ml of plasma to less than 50 copies/ml.

Given the dramatic effects of HAART, it was proposed that complete elimination of the virus might be possible within 2 to 3 years. However, even after long-term suppression of viral replication with HAART, the virus rapidly rebounds after therapy is discontinued. A key contributor to viral rebound appears to be a reservoir of latently+infected cells, including CD4 memory T cells. The half-life of the latently infected population is quite long, and it is estimated that it would take over 60 years of HAART to eliminate this population. Therefore, life-long HAART would be required to control infection in patients.

Retroviruses, including HIV-I, are RNA viruses that replicate through a DNA intermediate and integrate very efficiently into the genome of an infected cell forming a pro virus. Once the pro virus is formed, it is maintained in the genome of the infected cell and transferred to daughter cells in the same fashion as any other genetic element within the cellular genome. Thus, the virus has the potential to persist if it infects long-lived cells such as memory T cells. It has been known since 1986 that HIV-I can establish a latent infection in culture. It was found that a human T cell line infected with replication-competent virus could develop a latent infection in which the provirus was dormant but could be reactivated upon stimulation. Since then it has been established that a number of cytokines can reactivate latent proviruses.

The role that latency is playing in preventing clearance of the virus infection has become evident in recent years. Patients that had been successfully treated with HAART in which viral RNA was maintained at levels below 50 copies/ml in the plasma for years, experienced rapid virus rebound upon withdrawal of therapy. Moreover, it was found that after T cell activation, virus could be isolated from CD4 T cells taken from these patients making it clear that to eradicate the virus it will be necessary to eliminate the latently infected cells.

There have been attempts to flush the latent virus from infected individuals by nonspecific activation of T cells to "turn on" latent proviruses. As part of this approach, the patients remain on HAART to prevent new infections, and the infected cells from which the latent proviruses are activated should die due to cytotoxic effects of viral expression and/or because of targeting by the immune system which can recognize the cells once they begin to express the viral proteins.

Thus, there is a need in the art for further strategies to discover new drugs capable of activating latent viruses.

SUMMARY

Disclosed are methods for creating a population of cells latently infected with a virus comprising the steps of: a) isolating primary cells; b) priming the cells toward differentiation, wherein at least a portion of primary cells differentiate into non-polarized cells; c) exposing the non-polarized cells of step b) to a virus defective in Env; thereby creating a population of cells latently infected with a virus and wherein the Env is provided in trans to the env defective virus while the virus is being grown, prior to exposure to the non-polarized cells of step c.

Also disclosed herein are cell lines comprising non-polarized CD4+ cells that have been latently infected with a virus.

Also disclosed are methods of reactivating a cell latently infected with virus, the method comprising activating NFAT in the absence of NF-κB.

Also disclosed are methods of reactivating a cell latently infected with virus, the method comprising contacting the cell with IL-7 in the absence of NFAT.

Disclosed herein are methods of treating a subject with a retrovirus, the method comprising: a) exposing the subject to a composition that reactivates cells latently infected with a retrovirus; and b) treating the subject with an antiretroviral agent identified by a method disclosed herein.

Also disclosed are methods of screening for a composition that activates a cell latently infected by a virus; the method comprising the steps of: a) creating a latently infected cell; b) exposing the cell to a test composition; and c) determining if the latently infected cell becomes active.

Further disclosed are compositions identified by the screening method described above.

Also disclosed is an assay for determining a composition capable of reactivating a cell latently infected with a retrovirus, the assay comprising an in vitro population of cells latently infected with a retrovirus, wherein at least 5, 10, 15, 20, 25, 30, 35, 40, 45, 50, 55, 60%, or more of the cells are latently infected, and wherein the cell population is stable.

Also disclosed are kits for screening for compositions that reactivate a latently infected virus in a cell comprising cytokines, latently infected cells, and antibody.

BRIEF DESCRIPTION OF THE DRAWINGS

The accompanying drawings, which are incorporated in and constitute a part of this specification, illustrate several embodiments and together with the description illustrate the disclosed compositions and methods.

DETAILED DESCRIPTION

Figure 1:
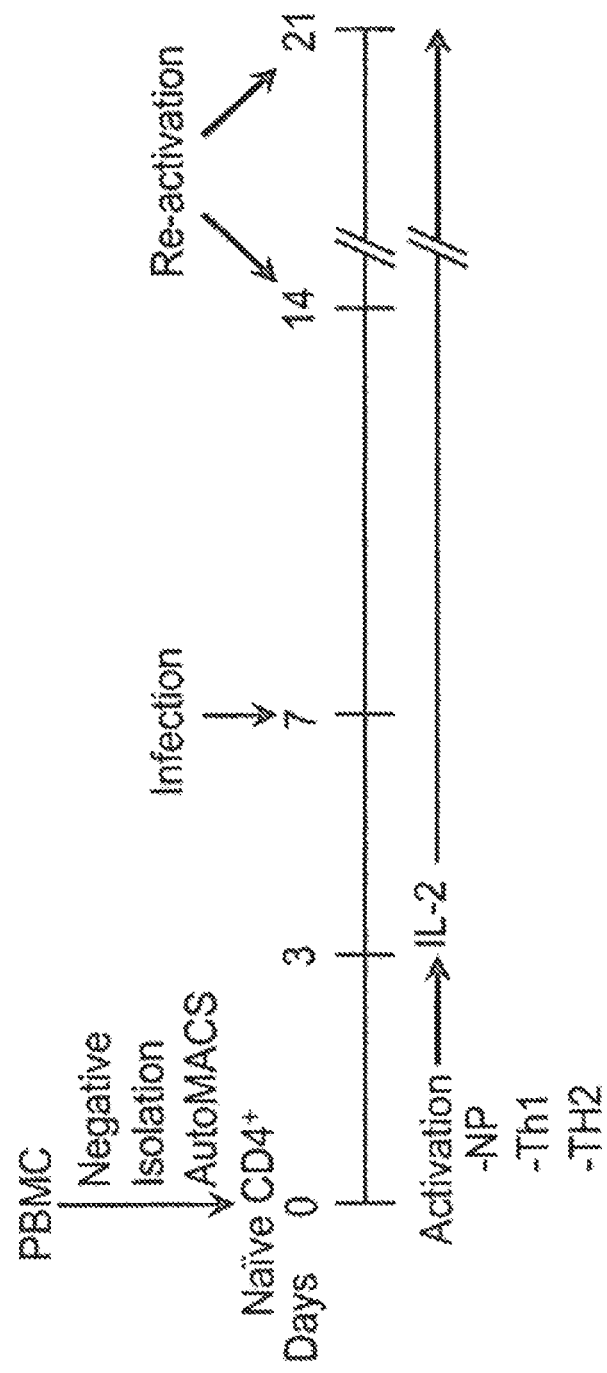
FIG. 1 shows a model of HIV-1 latency. Procedure used for the generation of human primary memory T cells and subsequent establishment of latent infections.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

By "inducible expression system" is meant a construct or combination of constructs that includes a nucleotide sequence encoding a transactivator, an inducible promoter that can be transcriptionally activated by the transactivator, and a nucleotide sequence of interest operably linked to the inducible promoter.

By "transactivator," "transactivating factor," or "transcriptional activator" is meant a polypeptide that facilitates transcription from a promoter. Where the promoter is an inducible promoter, the transactivator activates transcription in response to a specific transcriptional signal or set of transcriptional signals.

By "envelope protein" is meant a polypeptide that 1) can be incorporated into an envelope of a virus such as a retrovirus; and 2) can bind target cells and facilitate infection of the target cell by the RNA or DNA virus that it envelops. "Envelope protein" is meant to include naturally-occurring (i.e., native) envelope proteins and functional derivatives thereof that 1) can form pseudotyped retroviral virions, and 2) exhibit a desired functional characteristic(s) (e.g, facilitate viral infection of a desired target cell, and/or exhibit a different or additional biological activity) when provided in trans. Such envelope proteins include retroviral envelope proteins derived from any suitable retrovirus (e.g., an amphotropic, xenotropic, ecotropic or polytropic retrovirus) as well as non-retroviral envelope proteins that can form pseudotyped retroviral virions (e.g., VSV G). Envelope proteins of particular interest include, but are not limited to, envelope protein of vesicular stomatis virus (VSV G), HTLV-1, gibbon ape leukemia virus (GALV), Sindai virus, influenza virus, herpes virus, rhabdovirus, and rabies virus.

By "functional derivative of a polypeptide" is meant an amino acid sequence derived from a naturally-occurring polypeptide that is altered relative to the naturally-occurring polypeptide by virtue of addition, deletion, substitution, or other modification of the amino acid sequence. "Functional derivatives" contemplated herein exhibit the characteristics of the naturally-occurring polypeptide essential to the operation of the invention.

By "promoter" is meant a minimal DNA sequence sufficient to direct transcription of a DNA sequence to which it is operably linked. The term "promoter" is also meant to encompass those promoter elements sufficient for promoter-dependent gene expression controllable for cell-type specific expression, tissue-specific expression, or inducible by external signals or agents; such elements may be located in the 5' or 3' regions of the naturally-occurring gene.

By "inducible promoter" is meant a promoter that is transcriptionally active when bound to a transcriptional activator, which in turn is activated under a specific condition(s), e.g., in the presence of a particular chemical signal or combination of chemical signals that affect binding of the transcriptional activator to the inducible promoter and/or affect function of the transcriptional activator itself.

By "construct" is meant a recombinant nucleotide sequence, generally a recombinant DNA molecule, that has been generated for the purpose of the expression of a specific nucleotide sequence(s), or is to be used in the construction of other recombinant nucleotide sequences. In general, "construct" is used herein to refer to a recombinant DNA molecule.

By "operably linked" is meant that a DNA sequence and a regulatory sequence(s) are connected in such a way as to permit gene expression when the appropriate molecules (e.g., transcriptional activator proteins) are bound to the regulatory sequence(s).

By "operatively inserted" is meant that a nucleotide sequence of interest is positioned adjacent a nucleotide sequence that directs transcription and translation of the introduced nucleotide sequence of interest (i.e., facilitates the production of, e.g., a polypeptide encoded by a DNA of interest).

By "packaging cell line" is meant a line of packaging cells selected for their ability to package defective retroviral vectors at a titer of generally greater than $10^3$ virions per milliliter of tissue culture medium, having less than 10 helper virus virions per milliliter of tissue culture medium, and capable of being passaged in tissue culture without losing their ability to package defective retroviral vectors.

By "transformation" is meant a permanent or transient genetic change, preferably a permanent genetic change, induced in a cell following incorporation of new DNA (i.e., DNA exogenous to the cell). Where the cell is a mammalian cell, a permanent genetic change is generally achieved by introduction of the DNA into the genome of the cell.

By "target cell" is meant a cell(s) that is to be transformed using the methods and compositions of the invention. Transformation may be designed to non-selectively or selectively transform the target cell(s).

By "transformed cell" is meant a cell into which (or into an ancestor of which) has been introduced, by means of recombinant DNA techniques, a DNA molecule encoding a gene product (e.g., RNA and/or protein) of interest (e.g., nucleic acid encoding a therapeutic cellular product).

By "subject" or "patient" is meant any subject for which cell transformation or gene therapy is desired, including humans, non-human primates, cattle, dogs, cats, guinea pigs, rabbits, mice, insects, horses, chickens, and any other genus or species having cells that can be infected with a viral vector having an envelope containing VSV G or other envelope described herein.

By "transgenic organism" is meant a non-human organism (e.g., single-cell organisms (e.g., yeast), mammal, nonmammal (e.g., nematode or *Drosophila*)) having a non-endogenous (i.e., heterologous) nucleic acid sequence present as an extrachromosomal element in a portion of its cells or stably integrated into its germ line DNA.

By "transgenic animal" is meant a non-human animal, usually a mammal, having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

By "viral vector" is meant a recombinant viral particle that accomplishes transformation of a target cell with a nucleotide sequence of interest.

By "virion," "viral particle," or "retroviral particle" is meant a single virus minimally composed of an RNA or DNA genome, Pol protein (for reverse transcription of the RNA genome following infection), Gag protein (structural protein present in the nucleocapsid), and an envelope protein. As used herein, the RNA genome of the retroviral particle is usually a recombinant RNA genome, e.g., contains an RNA sequence exogenous to the native retroviral genome and/or is defective in an endogenous retroviral sequence (e.g., is defective in pol, gag, and/or env, and, as used herein, is normally defective in all three genes).

By "pseudotyped viral particle," or "pseudotyped retroviral particle" is meant a viral particle having an envelope protein that is from a virus other than the virus from which the RNA genome is derived. The envelope protein can be from a retrovirus of a species different from the retrovirus from which the RNA genome is derived or from a non-retroviral virus (e.g., vesicular stomatitis virus (VSV)).

By "VSV G" or "VSV G envelope protein" is meant the envelope protein of vesicular stomatitis virus (VSV) or a polypeptide derived therefrom or recombinant fusion polypeptide having a VSV G polypeptide sequence fused to a heterologous polypeptide sequence, where the VSV G-derived polypeptide of recombinant fusion polypeptide can be contained in a viral envelope of a pseudotyped retroviral particle and retains infectivity for a desired target cell (e.g., a range of desired eukaryotic cells, or a specific target cell of interest).

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Although embodiments have been depicted and described in detail herein, various modifications, additions, substitutions and the like can be made.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular notch structural motif is disclosed and discussed and a number of modifications that can be made to a number of molecules including the notch structural motif are discussed, specifically contemplated is each and every combination and permutation of notch structural motif and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

B. COMPOSITIONS AND METHODS

The use of antiretroviral therapy in human immunodeficiency virus type 1 (HIV-1) infected patients does not lead to virus eradication. This is due, to a significant degree, to the fact that HIV-1 can establish a highly stable reservoir of latently infected cells. In this work, an ex vivo experimental system that generates high levels of HIV-1 latently infected memory cells using primary CD4+ T cells is described. Use of this model enabled the dissection of the T cell-signaling pathways and characterization of the long terminal repeat (LTR) cis-acting elements involved in reactivation of HIV-1 in memory CD4+ T cells. The results of this study conclude that Lck and NFAT are required for optimal latent virus reactivation in memory T cells. It was also found that the cis-acting elements which are critical toward HIV-1 reactivation are the Sp1 and κB/NFAT transcription factor binding sites.

HIV-1 persists in infected individuals even in the presence of HAART. The principal reservoir of HIV-1 latency is thought to reside in resting, $CD4^+$ memory T cells, which harbor integrated HIV-1 (Finzi et al. 1997). The low frequency of latently infected cells (1 in $10^6$ resting $CD4^+$ T cells (Chun et al. 1997)), for which known phenotypic markers are not available, poses a great challenge to the study of latency in vivo.

Previous studies on HIV-1 latency were based on the generation of chronically infected cell lines, such as the ACH2 (Folks et al. 1989), JΔK (Antoni et al. 1994), and J-Lat (Jordan et al. 2003) T-cell lines, and the U1 promonocytic cell line (Folks et al. 1987). In these systems, latency was defined as a state in which integrated proviruses failed to drive efficient gene expression. However, these systems do not necessarily reflect the latency state in vivo because the lack of viral gene expression is due to mutations in tat (ACH2 and U1 (Folks et al. 1989, Folks et al. 1987)) or mutations in the LTR (JΔK T-cell line (Antoni et al. 1994)). While these latency models recapitulate a plethora of mechanisms that can underlie viral latency, the focus of this study was in developing a more general model that did not rely on clonal proviral integration sites, and which utilized non-transformed, primary human T-cells.

Recently, a model using human fetal liver tissue in SCID-hu mice has generated a great deal of interest in the field of HIV-1 latency (Brooks et al. 2001). This model relies upon infection of thymocytes and the vast majority of latently infected cells in this system are mature, quiescent CD4+ single positive naïve T cells. This is in contrast with findings in HIV-1 patients, where the majority of latently infected cells are CD4+ memory T cells (Finzi et al. 1997). Although naïve and memory cells, share the characteristic of being quiescent, a likely requirement for HIV-1 latency in T cells (Finzi et al. 1997), there are important differences between these cell types that impact latency and reactivation.

Disclosed herein is the development of a novel HIV-1 latency and reactivation models that use human, primary cells. This model is used to dissect relevant signaling pathways involved in viral reactivation from latently infected memory CD4+ cells.

1. Cell Cultures and Methods Thereof

In order to screen for agents that can reactivate latent virus in a cell, it is necessary to have a latently infected cell. While it is possible to conduct such screening in vivo, the ability to control reactivation is limited in said situations and can be very expensive. An in vitro method of screening for agents that induce reactivation of latently infected virus avoids the problems of in vivo systems and is vastly lest expensive. However, to create such a system requires the presence of a latently infect cell line. Therefore, disclosed herein is a method for creating a population of cells latently infected with a virus, the method comprising the steps of: a) isolating primary cells; b) priming the cells toward differentiation, wherein at least a portion of primary cells differentiate into non-polarized cells; c) exposing the non-polarized cells of step b) to a virus defective in Env; thereby creating a population of cells latently infected with a virus and wherein the Env is provided in trans to the env defective virus while the virus is being grown, prior to exposure to the non-polarized cells of step c.

Examples of retroviral-derived env genes which can be employed herein include, but are not limited to type C retroviral envelope proteins, such as those from Moloney murine leukemia virus (MoMuLV), Xenotropic murine leukemia virus-related virus (XMRV), Harvey murine sarcoma virus (HaMuSV), murine mammary tumor virus (MuMTV), gibbon ape leukemia virus (GaLV), and Rous Sarcoma Virus (RSV). Other viral env genes which can be used include, for example, env genes from immunodeficiency viruses (HIV-1, HIV-2, FIV, SIV and EIV), human T cell leukemia viruses (HTLV-1, HTLV-2, HTLV-3 and HTLV-4), herpes viruses (HSV-1, HSV-2, VZV, EBV, CMV, HHV-6, HHV-7, HHV-8), and Vesicular stomatitis virus (VSV) (Protein G). When producing recombinant retroviruses of the invention (e.g., recombinant lentiviruses), the wild-type retroviral (e.g., lentiviral) env gene can be used, or can be substituted with any other viral env gene, such those listed above. Methods of pseudotyping recombinant viruses with envelope proteins from other viruses in this manner are well known in the art. As referred to herein, a "pseudotype envelope" is an envelope protein other than the one that naturally occurs with the retroviral core virion, which encapsidates the retroviral core virion (resulting in a phenotypically mixed virus).

Viral envelope proteins of the invention (whether pseudotyped or not) can also be modified, for example, by amino acid insertions, deletions or mutations to produce targeted envelope sequences such as ecotropic envelope with the EPO ligand, synthetic and/or other hybrid envelopes; derivatives of the VSV-G glycoprotein. Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) PNAS 86:9079-9083; Julan et al. (1992) J. Gen Virol 73:3251-3255; and Goud et al. (1983) Virology 163:251-254); or coupling cell surface receptor ligands to the viral env proteins (Neda et al. (1991) J Biol Chem 266:14143-14146). Coupling can be in the form of the chemical cross-linking with a protein or other variety (e.g. lactose to convert the env protein to an asialoglycoprotein), as well as by generating fusion proteins (e.g. single-chain antibody/env fusion proteins).

The primary cells can be lymphocytes (e.g., CD4, CD8, and B cells), macrophages, dendritic cells, neurons, or epidermal cells. For example, the primary cell can be a CD4+ T-cell, such as naïve CD4 T-cells or a memory CD4+ T-cells (e.g., $T_{CM}$). It is understood that the type of primary cell depends on the latent reservoir of the virus for which reactivation is sought. Thus, for example, for HIV-1 or HIV-2, the primary cell is a CD4 T cell. By contrast, for EBV, the primary cell is a B cell and for HSV-1 and HSV-2, the primary cell is a neuron. It is understood that those of skill in the art will know the appropriate primary cell to establish latency for the given virus.

The virus can be any virus capable of producing latently infected cells. This includes, but is not limited to, retroviruses such as HIV-1, HIV-2, SIV, XMRV, HTLV-1, HTLV-2, HTLV-3 and HTLV-4 and herpesviruses such as Herpes Simplex virus 1 (HSV-1 also known as HHV-1), Herpes Simplex virus-2 (HSV-2 also known as HHV-2), Varicella Zoster virus (VZV); Epstein-Barr virus (EBV), Cytomegalovirus (CMV), Human Herpes virus-6 (HHV-6), Human Herpes virus-7 (HHV-7 also referred to as Roseolovirus), and Human Herpes virus-8 (HHV-8 also referred to as Karposi's sarcoma associated herpesvirus). The virus can also be hepatitis B or hepatitis C.

Retroviruses are enveloped RNA viruses that, after infection of a host cell, reverse transcribe their RNA genomes into a DNA intermediate, or provirus. All viruses containing an RNA genome and producing an RNA-dependent DNA polymerase are contained in the retroviral family. The family is divided into three subfamilies: (1) Oncovirinae, including all the oncogenic retroviruses, and several closely related non-oncogenic viruses; (2) Lentivirinae, the "slow retroviruses" such as the human immunodeficiency virus (HIV) and visna virus; and (3) Spumavirinae, the "foamy" retroviruses that induce persistent infections, generally without causing any clinical disease. Retroviruses containing at least three types of proteins encoded by the viral genome, i.e., gag proteins (the group antigen internal structural proteins), pol proteins (the RNA-dependent DNA polymerase and the protease and integrase proteins), and env proteins (the viral envelope protein or proteins). In addition to genes encoding the gag, pol, and env proteins, the genome to the retrovirus includes two long terminal repeat (LTR) sequences, one at the 5' and one at the 3' end of the virus. These 5' and 3' LTRs promote transcription and polyadenylation of viral mRNAs and participate in the integration of the viral genome into the cellular DNA of the host.

In the methods disclosed herein, a significant percentage of the population of infected cells can be latently infected. At least 5, 10, 15, 20, 25, 30, 35, 40, 45, 50, 55, or 60% or more of the population of cells can be latently infected.

Also disclosed herein is a cell line comprising non-polarized CD4+ cells (e.g., naïve or $T_{CM}$ cells) that have been latently infected with a virus. Similarly disclosed herein are cell lines comprising B cells, CD8 T cells (naïve or memory), macrophages, hepatocytes, epidermal cells, or neurons latently infected with a virus.

The virus can be any virus capable of producing latently infected cells. This includes, but is not limited to, retroviruses such as HIV-1, HIV-2, SIV, XMRV, HTLV-1, HTLV-2, HTLV-3 and HTLV-4. The virus can also be HSV-1, HSV-2, VZV, EBV, CMV, HHV-6, HHV-7, HHV-8, hepatitis C, or hepatitis B.

Also disclosed is a method of reactivating a cell latently infected with virus, the method comprising activating NFAT in the absence of NF-κB. Alternatively, also disclosed are methods of reactivating a cell latently infected with virus, the method comprising contacting a cell with IL-7 in the absence of NFAT. The reactivation can utilize the p38/MAP Kinase pathway. However, disclosed herein, the utilization of the p38/MAPK pathway can vary depending on the initial stimulus for reactivation. For example, in the case of a T cell, where reactivation is induced through stimulation of the TCR, then the p38/MAPK pathway involving NFAT is utilized. By contrast, reactivation of a latently infected cell via the use of IL-7 would use a p38/MAPK pathway that does not involve NFAT.

The virus can be any virus capable of producing latently infected cells. This includes, but is not limited to, retroviruses such as HIV-1, HIV-2, SIV and HTLV. The virus can also be hepatitis B or hepatitis C. NFAT can also be activated in the presence of CD3/CD28, or for example, can be activated in the presence of CD3/CD28 and Sp1.

The virus can be any virus capable of producing latently infected cells. This includes, but is not limited to, retroviruses such as HIV-1, HIV-2, SIV, XMRV, HTLV-1, HTLV-2, HTLV-3 and HTLV-4. The virus can also be HSV-1, HSV-2, VZV, EBV, CMV, HHV-6, HHV-7, HHV-8, hepatitis C, or hepatitis B.

Disclosed herein is a method of treating a subject with a retrovirus, the method comprising: a) exposing the subject to a composition that reactivates cells latently infected with a retrovirus; and b) treating the subject with an antiretroviral agent identified by a method disclosed herein.

As described above, highly active antiretroviral therapy (HAART) has had an important impact upon morbidity and mortality from AIDS. Although HAART results in a remarkable suppression of HIV-I replication in infected patients, it does not provide for elimination of the virus even after years of suppressive therapy. Complete viral clearance cannot be achieved due to the presence of latently infected cells in patients, which upon withdrawal of HAART, contribute to viral rebound. Attempts at eradicating latently infected cells by activating them with cytokines and lymphokines has not met with success probably owing both to the inability of this treatment to reach all of the latent viral reservoirs and to the toxicity of the regimen. Small molecules with pharmacological properties that allow them to reach all viral reservoirs and activate latent HTV-I pro viruses result in clearance of HIV-I infections when used in combination with HAART.

Disclosed herein is a latently infected cell line that can be used for high throughput screening (HTS) to identify small molecules that can be employed to eradicate latent virus from infected individuals.

2. Methods of Screening

The potential for viral latency to maintain a viral reservoir in a subject undergoing antiviral treatment necessitates that the subject never stops taking antivirals. By reactivating the virus while maintaining antiviral treatment, the viral reservoir can be depleted. However, identifying agents that accomplish the task of reactivating latent virus is difficult. Moreover, in vivo systems for reactivating a latent viral infection of difficult to manipulate or maintain a controlled system such that endogenous cytokines do not affect the outcome. Accordingly, an in vitro system for screening agents that reactivate latent viruses is need. Disclosed is a method of screening for a composition that activates a cell latently infected by a virus; the method comprising the steps of: a) creating a latently infected cell; b) exposing the cell to a test composition; and c) determining if the latently infected cell becomes active. It is understood and herein contemplated that the latently infected cell can be made by the methods disclosed herein.

It is further understood that the in addition to screening for an agent that activates a latently infected cell, disclosed herein are methods of screening for an agent that reactivates a latent virus in a latently infected cell. Thus, disclosed are methods of screening for a composition that reactivates latent virus in a cell latently infected by the virus; the method comprising the steps of: a) creating a latently infected cell; b) exposing the cell to a test composition; and c) determining if the virus in the latently infected cell becomes active. It is further understood that the disclosed methods of screening for an agent that reactivates a latent virus or activates a latently infected cell are not mutually exclusive methods and the same screen can arrive at both results.

The determination of cellular activation can be achieved through any means known in the art for determining cellular proliferation. For example, cellular activity can be measured by flow cytometry through the use of Carboxyfluorescein succinimidyl ester (CFSE), CD25, Ki-67, CD44. B220, CD69, loss of CD62L, or Propidium iodide. Additionally, cellular activation can be measured by 3H-Thymidine incorporation. Viral reactivation can be determined by any measuring technique known in the art, including but not limited to flow cytometry through the use of DsRed or HIV Gag p24, or using DNA measuring techniques such as quantitative PCR and methods that include the presence of a reporter gene within the virus genome, such as luciferase, beta galactosidase and GFP can also be utilized.

Further disclosed is a composition identified by the screening method described above. In one example, the cell can be further exposed to CD3/CD28 antibodies during step b). The cell can also be exposed to PHA during step b). The virus can be any virus capable of producing latently infected cells. This includes, but is not limited to, retroviruses such as HIV-1, HIV-2, SIV, XMRV, HTLV-1, HTLV-2, HTLV-3 and HTLV-4. The virus can also be HSV-1, HSV-2, VZV, EBV, CMV, HHV-6, HHV-7, HHV-8, hepatitis C, or hepatitis B.

Also disclosed is an assay for determining a composition capable of activating a cell latently infected with a virus or reactivating a latent virus, the assay comprising an in vitro population of cells latently infected with a retrovirus, wherein at least 5, 10, 15, 20, 25, 30, 35, 40, 45, 50, 55, 60%, or more of the cells are latently infected, and wherein the cell population is stable.

C. KITS

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include a cell assay of latent cells including cytokines or antibodies to aid activation or reactivation (e.g., IL-7, IL-2, αCD3/αCD28, IL-1, IL-10, IL-12, IL-15, IL-6, TNF-α, TGF-β, IFN-α and IFN-β), antibodies or other reagents to visualize the assay results (e.g., CFSE, CD25, Ki-67, CD44. B220, CD69, loss of CD62L, Propidium iodide, and/or p24) and instructions for utilizing the components. Furthermore, the kits can include frozen and expanded latently infected cells. Thus, for example, disclosed herein are kits comprising a latently infected CD4 T cell, CFSE, and IL-7. It is understood and herein contemplated that any antibodies supplied with the kit can be modified to incorporate a detectable label.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminesce. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson–; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5TM; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (DilC18(5)); DIDS; Dihydrorhodamine 123 (DHR); Dil (DilC18(3)); I Dinitrophenol; DiO (DiOC18(3)); DiR; DiR (DilC18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow SGF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-lndo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin EBG; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO 3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

A modifier unit such as a radionuclide can be incorporated into or attached directly to any of the compounds described herein by halogenation. Examples of radionuclides useful in this embodiment include, but are not limited to, tritium, iodine-125, iodine-131, iodine-123, iodine-124, astatine-210, carbon-11, carbon-14, nitrogen-13, fluorine-18. In another aspect, the radionuclide can be attached to a linking group or bound by a chelating group, which is then attached to the compound directly or by means of a linker. Examples of radionuclides useful in the apset include, but are not limited to, Tc-99m, Re-186, Ga-68, Re-188, Y-90, Sm-153, Bi-212, Cu-67, Cu-64, and Cu-62. Radiolabeling techniques such as these are routinely used in the radiopharmaceutical industry.

The radiolabeled compounds are useful as imaging agents to diagnose neurological disease (e.g., a neurodegenerative disease) or a mental condition or to follow the progression or treatment of such a disease or condition in a mammal (e.g., a human). The radiolabeled compounds described herein can be conveniently used in conjunction with imaging techniques such as positron emission tomography (PET) or single photon emission computerized tomography (SPECT).

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair. In this mode, the detecting antibody or detecting molecule should include the other member of the pair.

Other modes of indirect labeling include the detection of primary immune complexes by a two step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

D. PHARMACEUTICAL CARRIERS/DELIVERY OF PHARMACEUTICAL PRODUCTS

The compositions found by the methods disclosed herein which can be used for treating HIV by, for example, causing latently infected cells to reactivate, can be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

(1) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Formulations for topical administration may include transdermal patches. Coated condoms, gloves and the like may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Compositions for parenteral, intrathecal or intraventricular administration may include sterile aqueous solutions which may also contain buffers, diluents and other suitable additives.

In addition to such pharmaceutical carriers, cationic lipids may be included in the formulation to facilitate uptake. One such composition shown to facilitate uptake is Lipofectin (BRL, Bethesda Md.).

E. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1 a) Materials and Methods
(1) Reagents
The following reagents were obtained through the AIDS Research and Reference Reagent Program, Division of AIDS, NIAID, NIH: Human rIL-2 from Dr. Maurice Gately, Hoffman-La Roche Inc. (Lahm et al. 1985); integrase Inhibitor (118-D-24) (Svarovskaia et al. 2004); and Monoclonal Antibody to HIV-1 p24 (AG3.0) from Dr. Jonathan Allan (Simm et al. 1995).
(2) T Cells
Peripheral blood mononuclear cells were obtained from Leukopaks from unidentified, healthy donors. Naïve CD4+ T cells were isolated by MACS microbead negative sorting using the naïve T cell isolation kit (Milteny Biotec, Aurburn, Calif.). The purity of the sorted populations was always higher than 95% with a phenotype $CD4^+CD45RA^+$ $CD45RO^-CCR7^+CD62L^+CD27^+$.

Naïve T cells were primed with beads coated with anti-CD3 and anti-CD28 (Dynal/Invitrogen, Carlsbad, Calif.) as previously described (Messi et al. 2003). Proliferating cells were expanded in medium containing 30 IU/ml IL-2, replacing medium and IL-2 each 2 days.

(3) Virus Generation and Viral Infection
DHIV viruses were produced by transient transfection of HEK293T cells by calcium phosphate-mediated transfection (Zhu et al. 2001). To normalize infections, p24 was analyzed in virus-containing supernatants by ELISA (ZeptoMetrix Corporation, Buffalo, N.Y.). Cells were infected by spinoculation: $1\times10^6$ cells were infected with 500 ng/ml of p24 during 2 hours at 2900 rmp and 37° C. in 1 ml.

LTR mutants were generated by mutagenesis in DHIV using Quickchange II XL (Startagen, Cedar Creek, Tex.). Mutations were confirmed by sequencing (See Supplementary Methods on line for the list of primers used).

(4) Flow Cytometry Analysis
To phenotype the cells, $2.5\times10^5$ cells were stained with the following mAbs: phycoerythrin-conjugated (PE)-anti-CD4, PE-anti-CCR5, PE-anti-CD45RO, PE-anti-CD27, fluorescein isothiocyanate-conjugated (FITC)-anti-CCR7, FITC-anti-CD45RA or PE-anti-CXCR4 (Caltag, Burlingame, Calif.) followed by flow cytometric analysis in a FACSCalibur using the Cell Quest (Becton Dickinson, Mountain View, Calif.).

To assess intracellular p24-gag expression, $5\times10^5$ cells were fixed and permeabilized with Citofix/Cytoperm during 30 min at 4° C. (BD Biosciences, San Diego, Calif.). Cells were washed with Perm/Wash Buffer (BD Biosciences) and stained with 1:40 dilution of anti-p24 antibody (AG3.0) in 100 µl of Perm/Wash Buffer during 30 min at 4° C. Cells were washed with Perm/Wash Buffer and incubated with 1:100 Alexa Fluor 488 goat anti-mouse IgG (H+L) in 100 µl of Perm/Wash Buffer during 30 min at 4° C. Cells were washed with Perm/Wash Buffer and samples were analyzed by flow cytometry. Forward versus side scatter plots were used to define the live population. In all the experiments, HIV p24-gag staining regions were set with uninfected cells treated in parallel.

Apoptosis was evaluated by simultaneous determination of phosphatidylserine (PS) exposure and mitochondrial membrane potential ($\Delta\Psi_m$) in the same cells as previously described (Gomez-Benito et al. 2005).

(5) Reactivation Assays
$2.5\times10^5$ cells were reactivated with beads coated with anti-CD3 and anti-CD28 during 72 hours in the presence of IL-2 (1 bead per cell).

For inhibition studies, cells were preincubated with the indicated inhibitor for 2 hr before stimulation (See Supplementary Methods on line for the concentration of each inhibitor or activator).

(6) Integration Analysis
Genomic DNA from $10^6$ was isolated with the DNeasy Tissue Kit (Quiagen, Valencia, Calif.). 250 ng of genomic DNA were subjected to quantitative Alu-LTR PCR for integrated provirus as previously described (Vandegraaff et al. 2001, Butler et al. 2001, Dehart et al. 2005).

(7) Statistical Methods
Statistical analyses were performed with SPSS12.0 for Windows (SPSS Inc., Chicago, Ill.). Two-tailed Paired- Samples T test analysis was used to calculate the p value ($\alpha$=0.05). Error bars in box-plots represent range.

b) Results (1) A Novel Ex Vivo Paradigm to Study HIV-1 Latency

In order to recapitulate the generation of memory cell ex vivo, human, primary naïve CD4$^+$ T cells were isolated using negative selection (Miltenyi Biotec, Auburn, Calif.; FIG. 1). The naïve cells were then primed toward differentiation into non-polarized (NP), T helper-1 (Th1) or T helper-2 (Th2) as previously described (Messi et al. 2003).

Figure 6:
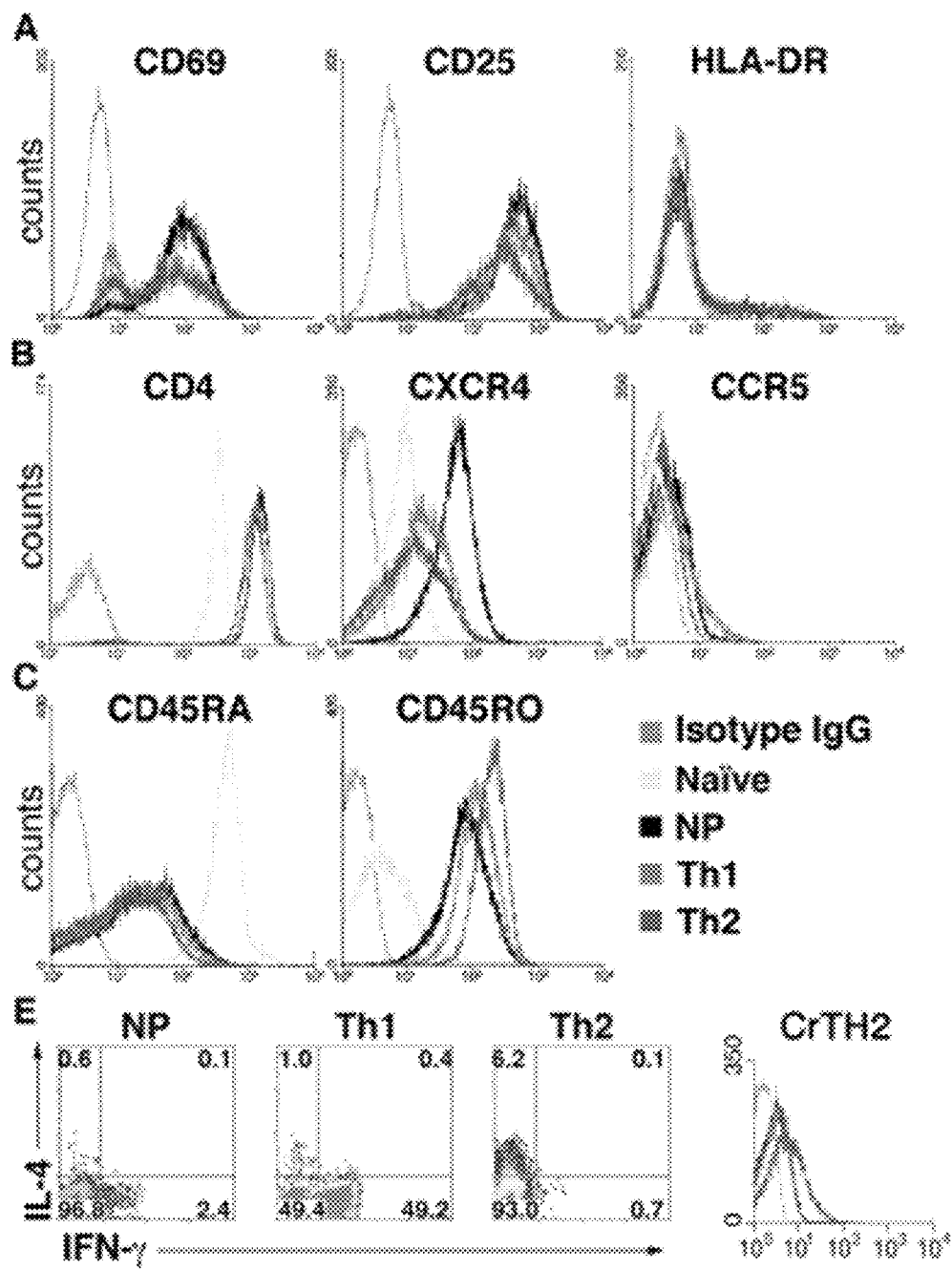
FIGS. 6A-6E show Phenotypic analysis of T cells. Naïve cells were primed in NP, Th1- or Th2-polarizing conditions and were subject to an extensively phenotypic analysis. Data are representative of analysis performed with 5 different donors. (A) Activation of naïve T cells led to expression of the activation markers, CD69, CD25 and HLA-DR: CD69 (early activation marker) and CD25 (medium-time activation marker) were analyzed 3 days after activation. HLA-DR (late activation marker) was analyzed 7 days after activation. (B) HIV-1 receptor, CD4, and co-receptors, CXCR4 and CCR5, were analyzed at the time of infection (7 days after activation) and compared with naïve cells. (C) CD45RA and CD45RO were analyzed at the time of infection and compared with naïve cells. The subset analyzed by each marker is indicated between parentheses. (D) Cells were analyzed for the expression of CCR7 and CD27, surface markers expressed in naïve and central memory T cells at day 0, 7, 14 and 21-post activation. (E) The phenotype of Th1 and Th2 cells was confirmed via intracellular staining for IFN-γ and IL-4, respectively 7 days after activation. On day 7, cells were restimulated with PMA plus Ionomycin for 1 h plus an additional 3 h in the presence of brefeldin A for intracellular cytokine detection. Also, cells were analyzed for the expression of CrTH2, surface marker expressed in Th2.
Figure 6:
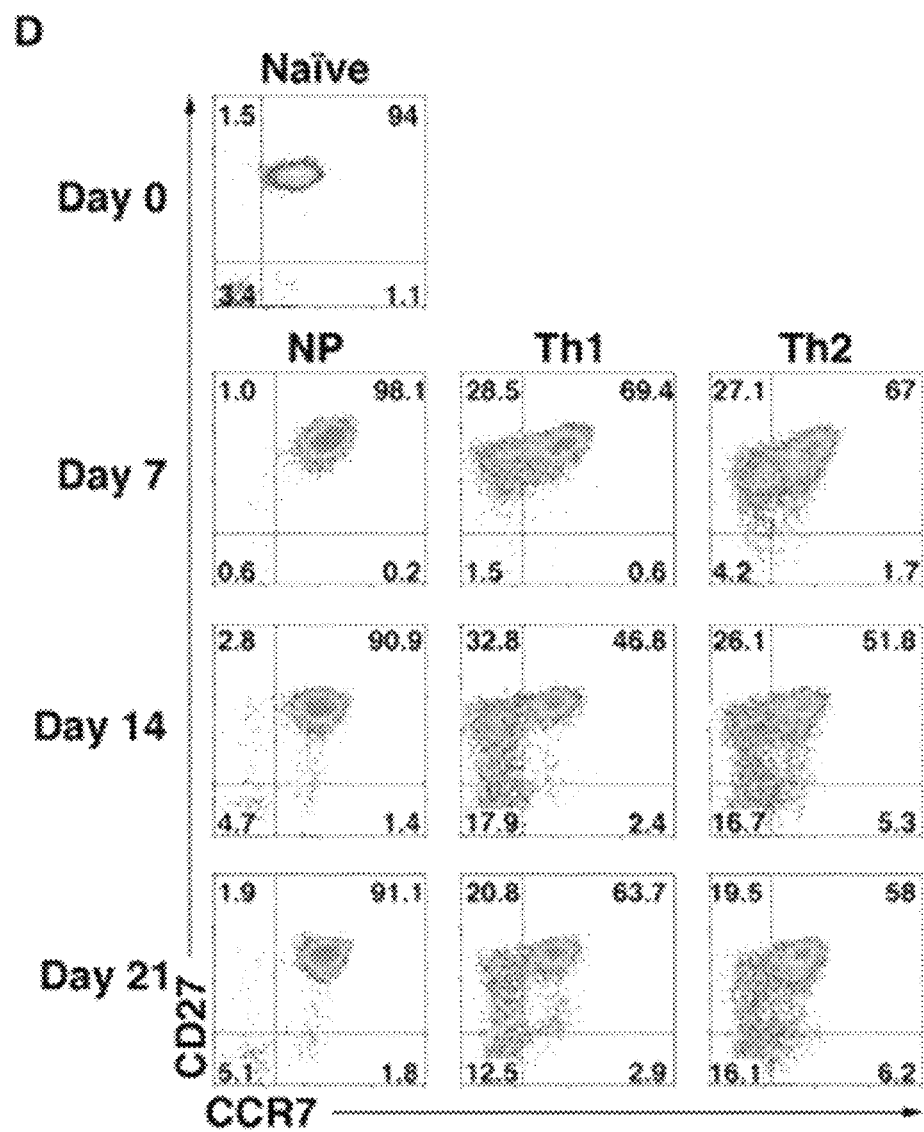

Phenotypic analysis confirmed the nature of the populations obtained in vitro (FIG. 6). In vivo, memory CD4$^+$ T cells fall into two main categories, central memory ($T_{CM}$) and effector memory ($T_{EM}$). The transcriptional profile of in vivo $T_{CM}$ closely resembles that of in vitro T cells stimulated in NP conditions (Messi et al. 2003, Rivino et al. 2004). Specifically, both $T_{CM}$ and NP cells are characterized by simultaneous expression of CCR7 (a homing receptor for secondary lymphoid tissues) and CD27 (a coactivation molecule) (Messi et al. 2003, Rivino et al. 2004). Expression of CCR7 and CD27 is also found on naïve cells, but is absent in $T_{EM}$. The analysis of CCR7 and CD27 expression in the cells was conducted at 0 (naïve), 7, 14 and 21 days after initial activation (FIG. 6). As expected, naïve CD4$^+$ T cells expressed high levels of CCR7 and CD27, as did cells primed in NP conditions. In contrast to NP, priming under Th1- and Th2-polarizing conditions led to loss of CCR7 and CD27 expression, and generated populations with phenotypes that were characteristic of both $T_{EM}$ cells and $T_{CM}$ cells (FIG. 6).

At day 7, cells from NP, Th1 and Th2 conditions were exposed to virus. A unique aspect of the model presented here is that the virus used in this model, DHIV (Andersen et al. 2006), has a small out-of-frame deletion in the gp120-coding area that renders it defective in Env. To produce virus by transfection, HIV-1 Env is provided in trans in a separate plasmid (Challita-Eid et al. 1998). Due to the higher expression levels of CXCR4 compared to CCR5 after the cells were activated (FIG. 6), a vector that consisted of the DHIV backbone pseudotyped with HIV-1$_{LAI}$ (an X4-tropic virus) Env was produced. The engineered defect in Env in DHIV precludes the production of infectious progeny after a single round of infection and thus the virus is unable to spread and cause massive cell death, which obscures the emergence of latency in vitro.

Figure 2:
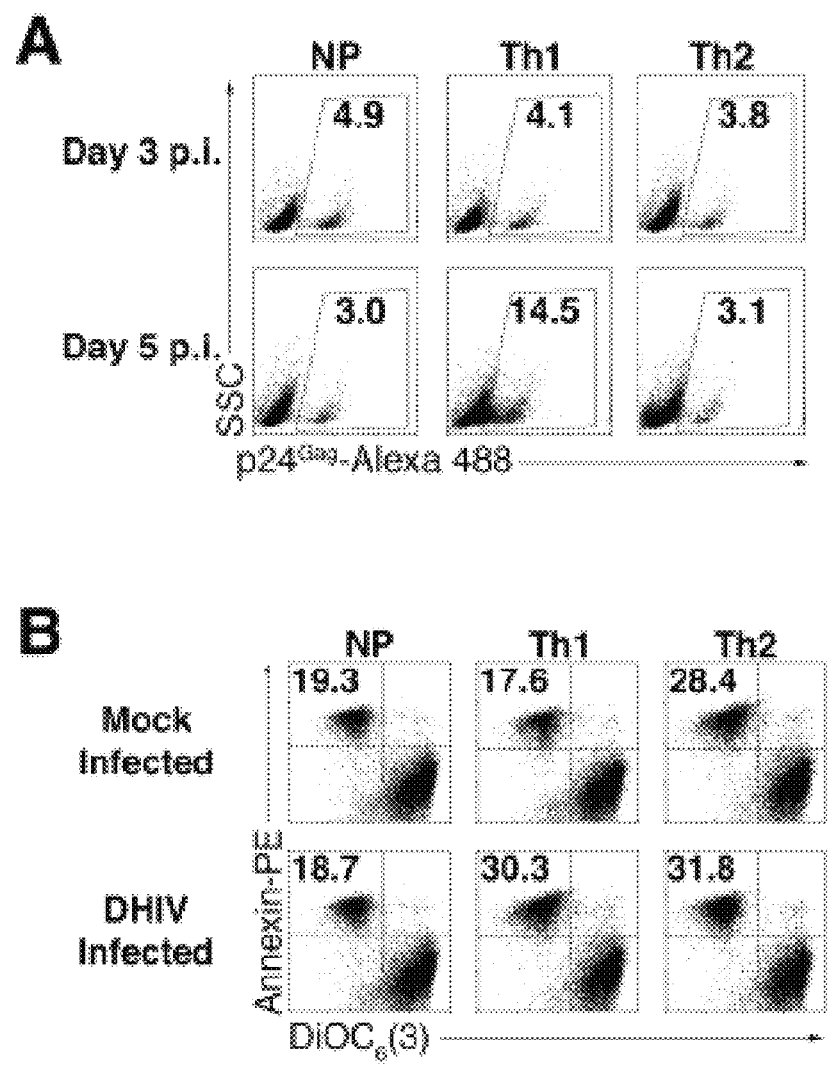
FIGS. 2A, 2B, 2C, 2D, and 2E show a generation of Latently HIV-1 infected primary CD4+ T cells ex vivo. Cells were primed in NP, Th1- or Th2-polarizing conditions and 7 days after activation cells were infected with DHIV. (A) 3 and 5 days p.i. cells were assessed for intracellular p24 gag expression by flow cytometry. The percentage of p24-positive cells is indicated in each panel. The experiment shown is representative of 4 different experiments with 4 different donors. (B) 5 days p.i. cells were assessed for annexin-PE and $DiOC_6(3)$ by flow cytometry. For each panel, the percentage of apoptotic cells (annexin-PE positive and $DiOC_6(3)$ low) is indicated. The experiment shown is representative of 3 different experiments with 3 different donors (C) 7 days after infection cells were cultured without stimulation (untreated) or co-stimulated with antibodies to CD3 and CD28 for 3 days (CD3/CD28) and assessed for intracellular p24 gag expression by flow cytometry. The percentage of p24-positive cells is indicated in each panel for this representative experiment. Values corresponding to 7 different donors are shown in (D), where each symbol represents a different donor and horizontal lines indicate media values. Significance by two-tailed Paired-Samples T test analysis (p values provided). (E) Viral integration was analyzed by Alu-PCR 3 days p.i. in Donors 1 and 2. Horizontal lines indicate median values.

Once infected, cells were kept in culture in the presence of IL-2, and infection levels were estimated via intracellular expression of p24$^{Gag}$ at days 3 and 5 post infection (p.i.). Intracellular p24$^{Gag}$ staining detects de novo produced viral Gag protein, indicative of a productive viral infection. The maximal level of p24$^{Gag}$ expression was observed 5 days p.i., and this level was highest in Th1 cells (FIG. 2A, lower panels). Mock infected cultures displayed <0.5% background in intracellular p24$^{Gag}$ staining.

At day 5 p.i., apoptosis levels were measured by flow cytometry. Positive staining for annexin V and low for DiOC$_6$(3) revealed the presence of apoptotic cells (FIG. 2B). Apoptosis levels in DHIV-infected NP and Th2 cells were similar to those in mock-infected cells. In contrast, apoptosis in DHIV-infected Th1 cells was high. The higher level of apoptosis in Th1 (12.7% over mock) was in agreement with the higher level of productive infection measured in these cells (14.5%) relative to other subsets.

Figures 2C, 2D, 2E:
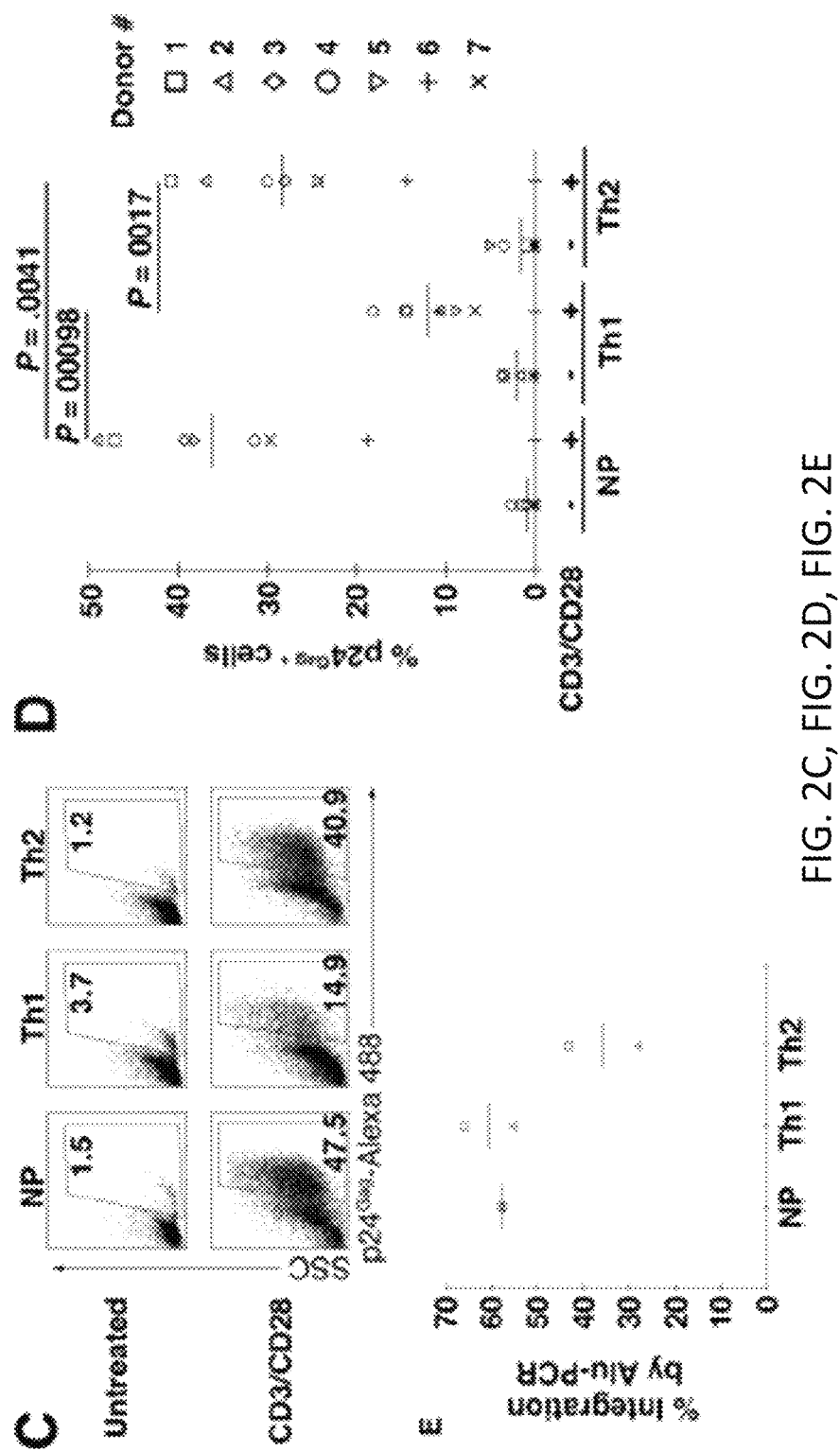

In order to induce reactivation of potential latent viruses, at day 7 p.i., cells were restimulated for 3 days in the presence of beads coated with αCD3 and αCD28 antibodies (FIG. 2C, CD3/CD28). As a negative control, parallel cultures were incubated in the absence of beads (FIG. 2C, untreated). Low levels of p24$^{Gag+}$ cells were detected in the absence of restimulation (FIG. 2C, upper panels). However, restimulation led to an increase in the percentage of p24$^{Gag+}$ cells in all subsets (FIG. 2C, lower panels). Remarkably, levels of p24$^{Gag+}$ cells after reactivation were higher in NP cells than in Th1 or Th2.

The results shown in FIG. 2C correspond to a single blood donor (Donor 1). To verify the generality of these findings in a broader population, further experiments were performed with 6 additional donors. The results, summarized in FIG. 2D, confirm that NP cells and, to a lesser degree, Th2-polarized cells, can harbor high levels of HIV-1 latency, whereas Th1-polarized cells display lower levels of latency.

Quantitative Alu-PCR was used to evaluate the levels of viral infection by a method that is independent of viral gene expression (Vandegraaff et al. 2001, Butler et al. 2001, Dehart et al. 2005). Quantitative Alu-PCR is specific for integrated viral DNA and detects latent and productive infections with the equal efficiency. Alu-PCR was performed at day 3 p.i. for two Donors 1 and 2 (FIG. 2E). Alu-PCR results for Donor 1 (square symbols) correspond to FIGS. 2A, C and D and show that the levels of integrated viruses in all three cell subsets greatly exceeded the frequency of p24$^{Gag+}$ cells that were observed at days 3 or 5 p.i. These results indicate that this method leads to highly efficient generation of latently infected cells.

Th1 populations consistently contained lower levels of p24$^{Gag+}$ cells than Th2 or NP upon reactivation. In addition, Th1 cells displayed levels of infection by Alu-PCR that were roughly equivalent or higher (FIG. 2E) than those seen in Th2 or NP. Therefore, it appears that Th1 cells are able to sustain higher levels of initial productive infection (i.e., p24$^{Gag+}$; FIG. 2A, day 5 p.i), followed by higher levels of apoptotic death, leading to less frequent latent infections.

Figure 7:
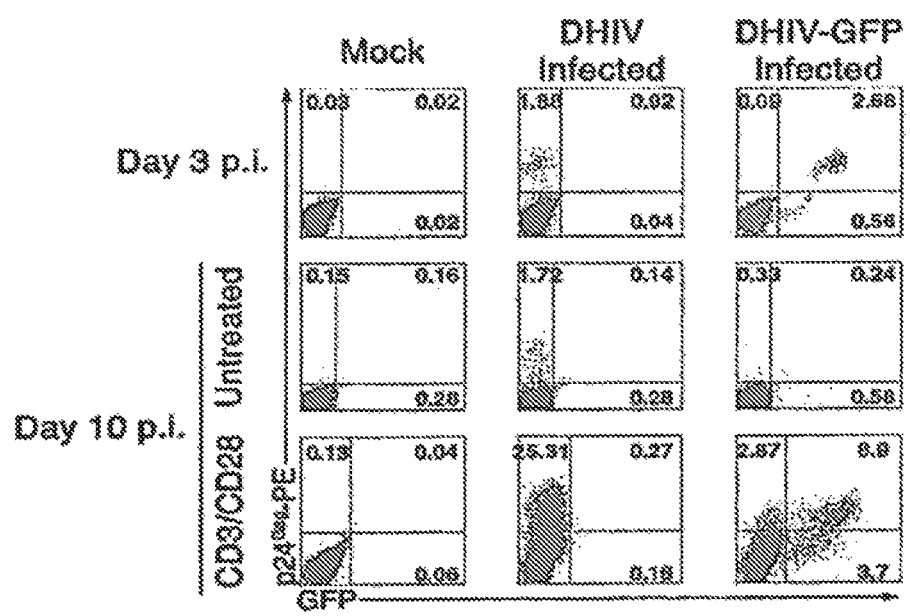
FIG. 7 shows p24 Gag intracellular staining correlates with GFP expression. Cells were primed in NP conditions and 7 days after activation cells were non-infected (Mock), infected with DHIV (DHIV Infected) or infected with a DHIV in which nef has been replaced by GFP (DHIV-GFP Infected). 3 days after infection cells were assessed for intracellular p24 Gag and GFP expression by flow cytometry. 7 days after infection cells were cultured without stimulation (untreated) or co-stimulated with antibodies to CD3 and CD28 for 3 days (CD3/CD28) and assessed for intracellular p24 Gag and GFP expression by flow cytometry. The percentage of cells is indicated in each panel for this representative experiment.

Detection of viral gene expression can also be accomplished via reporter molecules, such as GFP, with high sensitivity and specificity (Jordan et al. 2003). To test whether the latency and reactivation system produce similar results when using GFP as a reporter, parallel infections were performed with DHIV/X4 and DHIV-GFP/X4 (FIG. 7). In DHIV-GFP, nef had been replaced by the enhanced green fluorescent protein gene (Jordan et al. 2003). Aside from the nef replacement with GFP, DHIV-GFP is identical to DHIV. Most GFP-positive cells were also positive for p24, and vice versa, both during the initial infection and also after reactivation (FIG. 7). A small population of cells that are positive for GFP but negative for p24 can also be appreciated. These cells are, presumably, early in the infection or reactivation process and have not begun to produce viral late proteins. Therefore, intracellular p24 detection and GFP fluorescence can be used interchangeably in order to detect viral gene expression in this latency and reactivation model.

(2) Signaling Pathways Involved in HIV-1 Reactivation in TCM

Previous studies on cells from infected patients showed that central memory CD4$^+$ cells contain the highest frequency of HIV-1 DNA, on average 10 times higher than that of effector memory cells (Brenchley et al. 2004). Based on transcriptional profiles, cytokine production, surface phenotype, and the ability to differentiate into effector memory cells upon secondary antigenic challenge, NP cells are considered the in vitro equivalent of $T_{CM}$ (Messi et al. 2003). Therefore, further studies were focused on latent infection and reactivation of NP cells.

Figure 3:
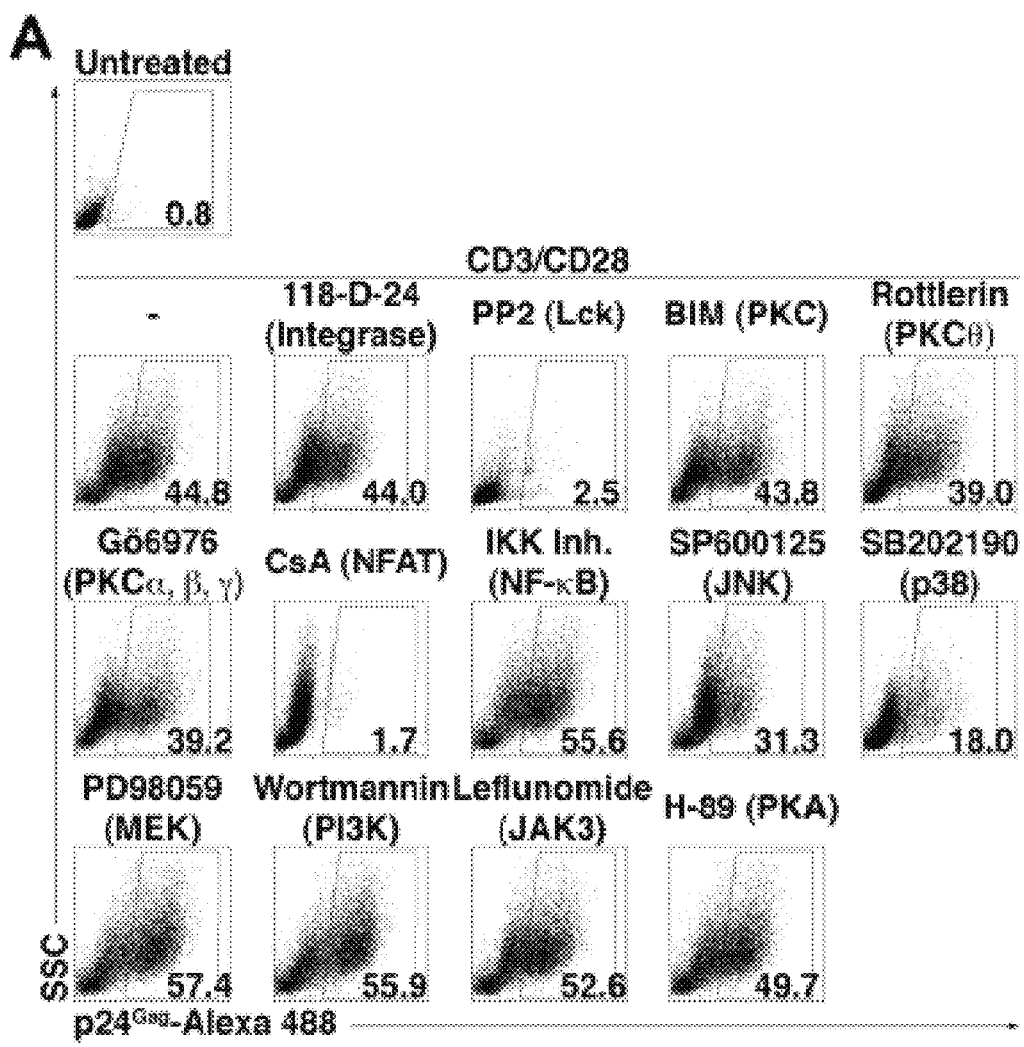
FIGS. 3A and 3B show the signaling pathways leading to HIV-1 reactivation I. NP cells were infected with DHIV and 7 days after infection cells were left untreated or co-stimulated with antibodies to CD3 and CD28 for 3 days (CD3/CD28) in the presence of the indicated inhibitor for the protein or pathway indicated between parentheses and assessed for intracellular p24 gag expression by flow cytometry. (A) Representative experiment. The percentage of p24-positive cells is indicated in each panel. (B) Box-plots corresponding to 3 different donors. Horizontal lines indicate median values and significance by two-tailed Paired-Samples T test analysis (p values provided).
Figure 3:
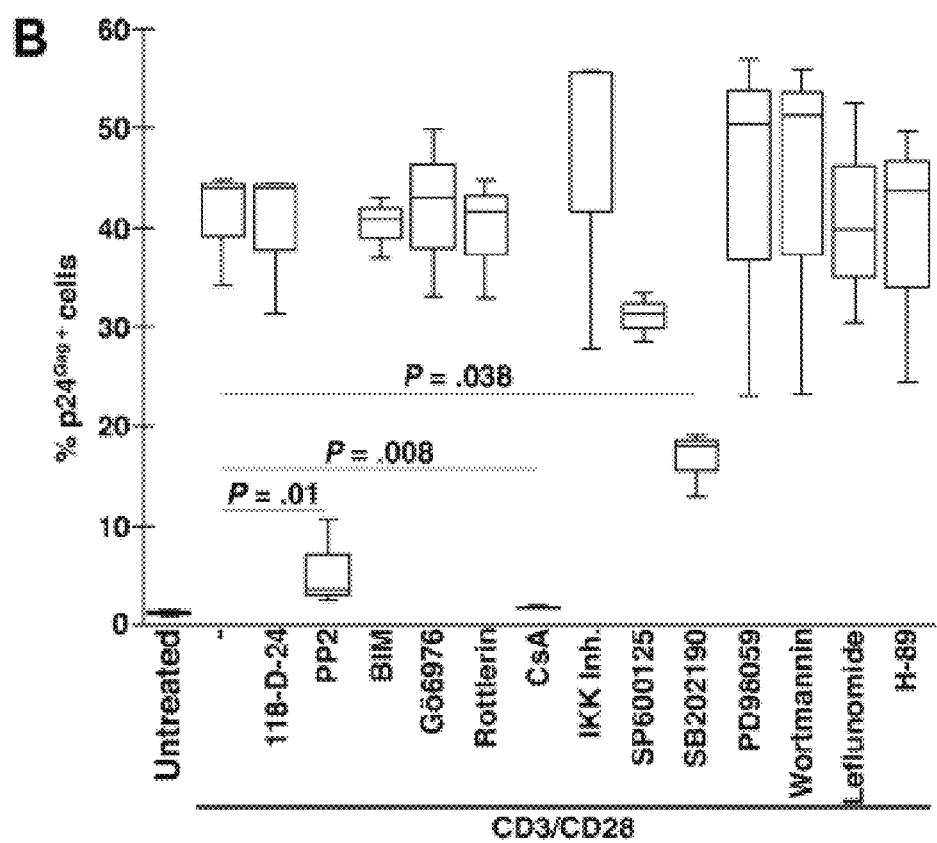

To begin to dissect potential signaling pathways leading to virus reactivation, a panel of known signaling inhibitors was tested. DHIV-infected NP cells were reactivated with αCD3/CD28, as shown in FIG. 2C, in the presence or absence of pharmacological inhibitors (FIG. 3). As a control, and to confirm expectations that the observed latent infections represent post-integration events, the integrase inhibitor, 118-D-24, was tested (FIG. 3A). As expected, 118-D-24 did not have any negative effect on viral reactivation.

One of the proximal events after activation of T cells through CD3 and CD28 is activation of the tyrosine kinase, Lck (see FIG. 8) (for a review, see (Kane et al. 2000)). Blocking Lck activation with PP2 abrogated HIV-1 reactivation by about 96% (inhibition of reactivation=(1−[p24% with αCD3/CD28 plus inhibitor−p24% untreated]/[p24% with αCD3/CD28−p24% untreated]×100; FIG. 3A). Lck activation leads to PLCγ1 activation and production of the second messengers, diacylglycerol (DAG) and inositol 1,4,5-triphosphate (IP3). DAG activates various isoforms of protein kinase C (PKC) (Isakov, 1987). Specifically in T cells, PKCθ leads to phosphorylation and degradation of IκB, with the subsequent release and nuclear translocation of the transcription factor, NFκB (Bauer et al. 2000). The DAG-PKC-NFκB signaling axis was probed by restimulating cells in the presence or absence of the general PKC inhibitor, BIM; an inhibitor of the classic isoforms of PKC (α, β and γ), Gö6976 was also tested; as well as Rottlerin, a specific inhibitor of PKCθ. None of these three compounds had a negative effect on viral reactivation (FIG. 3A). The IκB kinase peptide inhibitor (IKK inh) was used to confirm the previous result (Swaroop et al. 2001). When cells were reactivated in the presence of IKK inh, the levels of viral reactivation were not affected.

DAG also activates the Ras guanyl-nucleotide-releasing protein (RasGRP) (Lin et al. 2001). RasGRP and many isoforms of PKC activate Ras, leading to subsequent activation of the mitogen-activated protein (MAP) kinases, Erk1/2 (MEK), JNK, and p38. Inhibition of JNK or Erk1/2 with SP600125 or PD98059, respectively were used to probe the DAG-Ras-MAPK axis. Neither SP600125 nor PD98059 inhibited viral reactivation. In contrast, an inhibitor of p38, SB202190, significantly diminished (66% inhibition; FIG. 3A) HIV-1 reactivation.

The other second messenger generated by PLCγ1, IP3, activates calcineurin, which dephosphorylates and activates the transcription factor, NFAT (Lin et al. 2001). To probe the IP3-dependent signaling cascade, restimulation was conducted in the presence or absence of the calcineurin inhibitor, cyclosporine A (CsA). CsA completely abolished (99.9%) viral reactivation (FIG. 3A).

Figure 8:
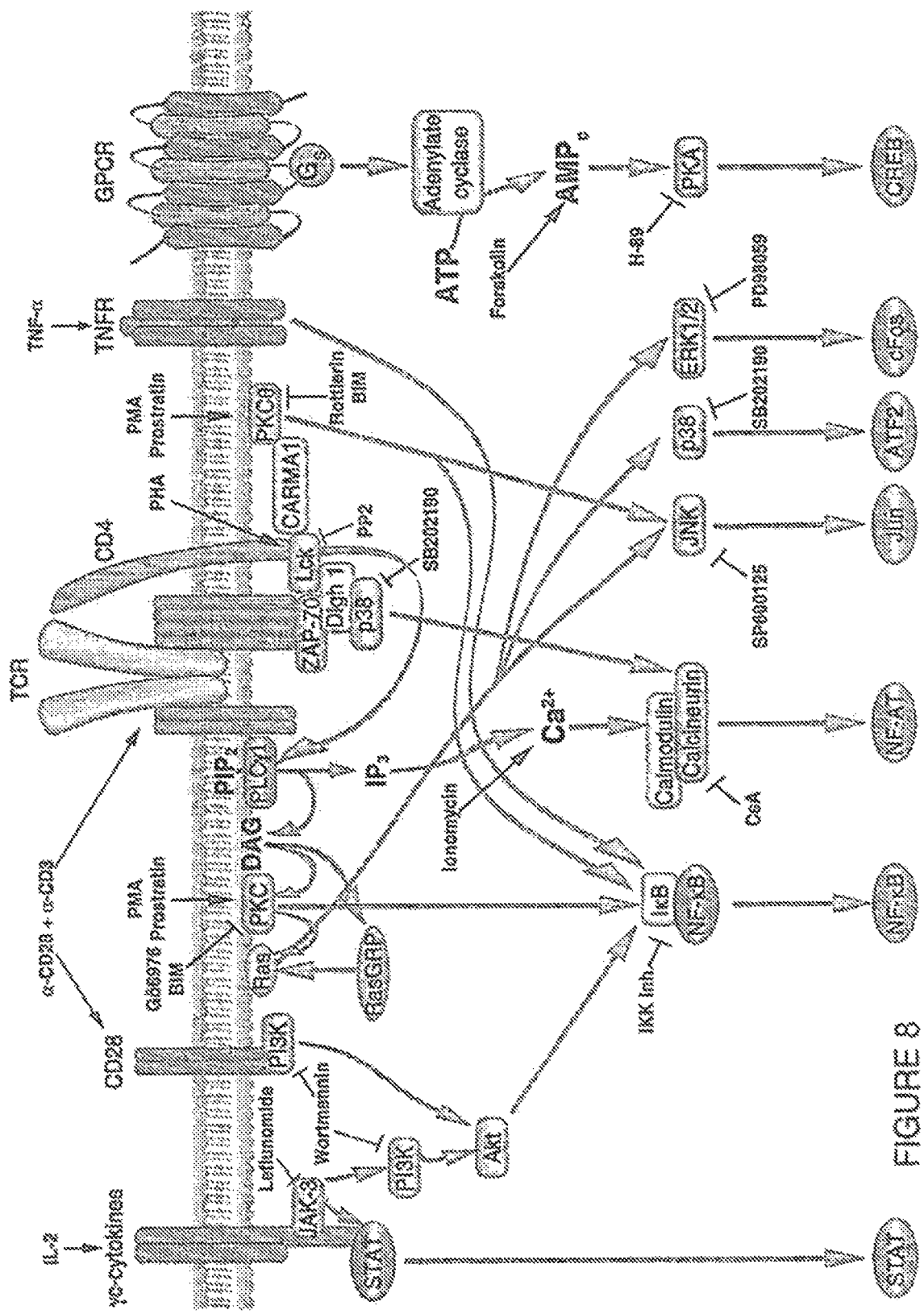
FIG. 8 shows T cell signaling. Diagram to describe the main T signaling pathways analyzed in this work. The inhibitors and agonist used in this work are represented with red letters or green letters, respectively.

Stimulation through CD3/CD28 also involves recruitment and activation of PI3K, leading to activation of the serine/threonine kinase, Akt (Franke et al. 1995). PI3K is also involved in signal transduction downstream of γc cytokine receptor engagement (FIG. 8). In order to ascertain the possible contribution of PI3K, Wortmannin, a PI3k inhibitor was tested. Incubation with Wortmanin had no effect on HIV-1 reactivation. Leflunomide, the Janus-activated kinase-3 (JAK3) inhibitor, was also tested to confirm the results with the γc cytokine-dependent pathway. Leflunomide also failed to block viral reactivation.

Signaling cascades in T cells can also be initiated through engagement of G protein-coupled receptors (GPCR; FIG. 8). GPCR signals typically converge in the production of cyclic AMP (cAMP), which activates protein kinase A (PKA), leading to the activation of the transcription factor CREB (for a review, see (Nordheim et al. 1994)). Cells were incubated with the PKA inhibitor, H-89, which did not have any effect on viral reactivation (FIG. 3A).

The above experiments with inhibitors were performed with two additional donors. The results with Donors 1, 3 and 4, summarized in FIG. 3B, denote striking similarities in the sensitivity of virus reactivation to drug inhibition across different individuals.

Figure 4:
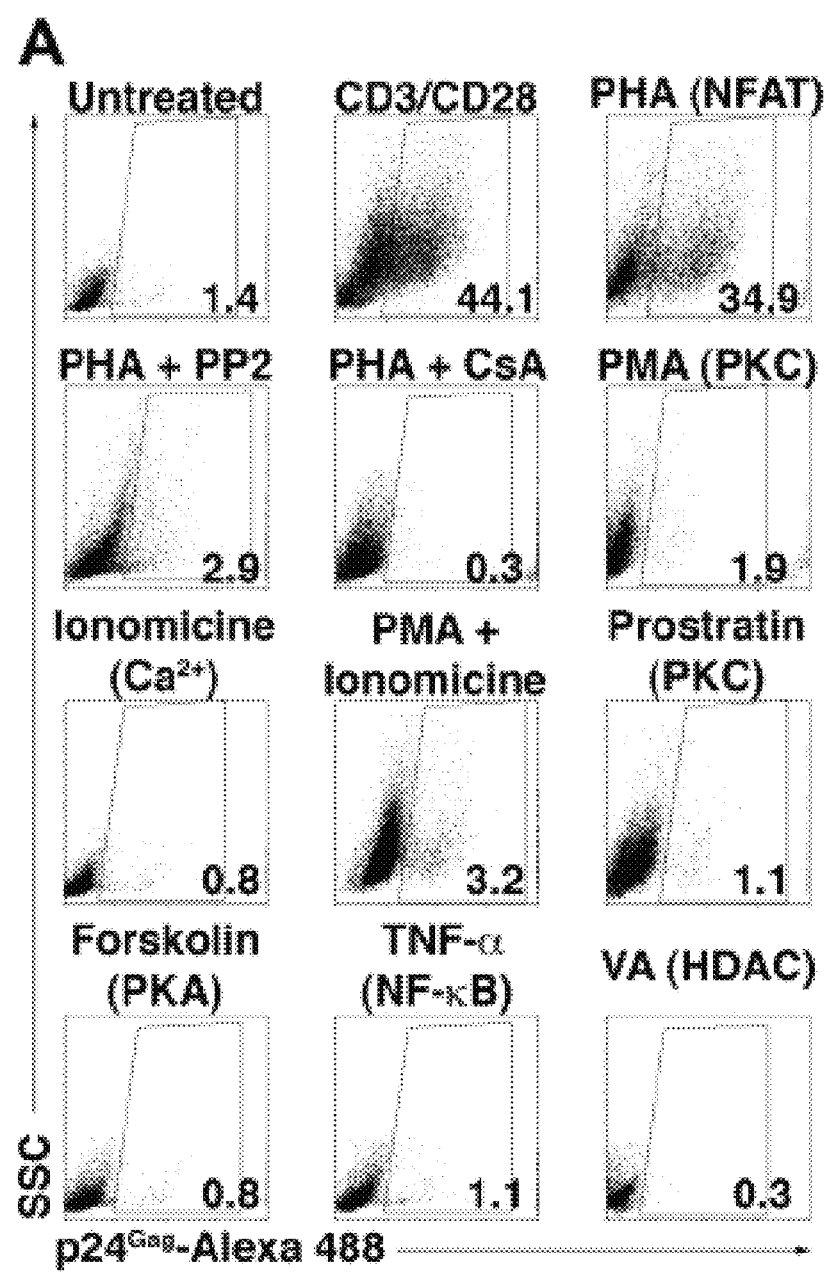
FIGS. 4A and 4B show signaling pathways leading to HIV-1 reactivation II. NP cells were infected with DHIV and 7 days after infection cells were left untreated, co-stimulated (CD3/CD28) or in the presence of the indicated agonist for the protein or pathway indicated between parentheses for 3 days and assessed for intracellular p24 gag expression by flow cytometry. In the case of cells stimulated with PHA, cells were also co-stimulated in the presence of the inhibitors PP2 (Lck) or CsA (NFAT). (A) Representative experiment. The percentage of p24-positive cells is indicated in each panel. (B) Box-plots corresponding to 3 different donors. Horizontal lines indicate median values and significance by two-tailed Paired-Samples T test analysis (p values provided).
Figure 4:
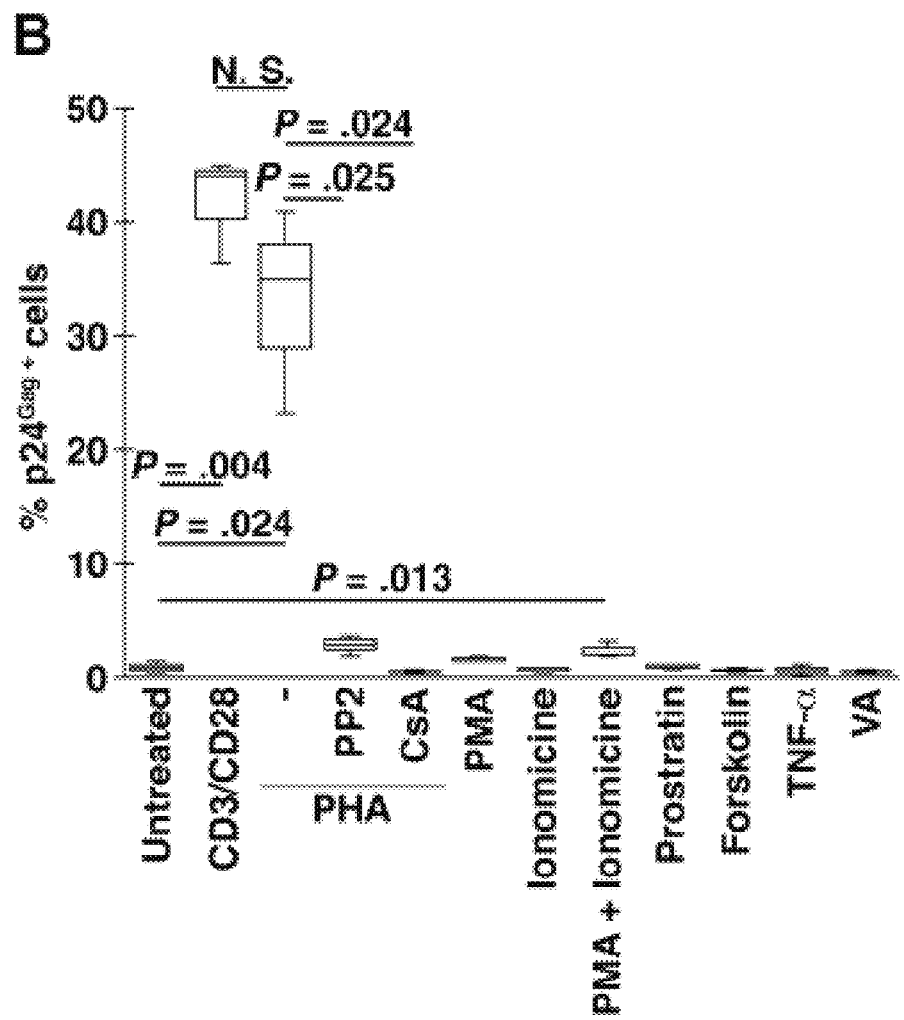

To complement the inhibitor studies, additional experimentation was conducted using agonists for the above signaling pathways. Latently infected cells were either left untreated or incubated with agonist. As a positive control, cells were treated with αCD3/CD28. The ability of the agonist to promote viral reactivation was then evaluated by detection of intracellular p24$^{Gag}$ as shown above (FIG. 4). Phytohemagglutinin (PHA), a lectin that binds non-specifically to carbohydrate moieties on surface glycoproteins and acts as a potent polyclonal mitogen for T cells, was the first to be tested. PHA incubation efficiently reactivated viral gene expression (79%; reactivation efficiency=([p24% with agonist−p24% untreated]/[p24% with αCD3/CD28−p24% untreated]×100; FIG. 4A). the effect of PHA on T cells are mediated by NFAT activation (FIG. 8). To confirm the role of NFAT in PHA-mediated reactivation, cells were co-incubated with PHA and the Lck inhibitor, PP2, or the calcineurin inhibitor, CsA. PHA stimulation in the presence of PP2 or CsA resulted in extremely low viral reactivation (3% and 0%, respectively). These results are in complete agreement with those from inhibitor studies and confirm the central role of NFAT in HIV-1 reactivation in memory T cells.

To activate the DAG-PKC-NFκB signaling axis, PMA and prostratin (both direct activators of PKC) were used separately. Neither compound was able to reactivate viral gene expression (FIG. 4A).

Signaling downstream of IP3 involves an increase in intracellular levels of calcium. To directly stimulate calcium influx, cells were incubated with Ionomycin, which had no effect on viral reactivation. However, a combination of PMA and Ionomycine was able to induce minor, but significant, levels of reactivation (4%).

In agreement with the lack of effect of H-89 (an inhibitor of PKA; FIG. 3A), incubation of cells with the PKA activator, forskolin, failed to reactivate virus gene expression.

In tumor cell lines harboring integrated, latent HIV-1 TNF-α can induce viral gene expression through the activation of NFκB (Folks et al. 1989, Jordan et al. 2003, Osborn et al. 1989, Duh et al. 1989). The potential role of TNF-α in virus reactivation in latently infected memory T cells was tested and it was found that TNF-α failed to induce any degree of viral gene expression (FIG. 4A).

Inhibition of histone deacetylases (HDAC) with valproic acid (VA) has previously been shown to induce viral reactivation (Ylisastigui et al. 2004, Simon et al. 1994, Lehrman et al. 2005). In the latent infection system, however, incubation with VA failed to reactivate viral gene expression (FIG. 4A).

As with the inhibitor studies, results with signaling pathway agonists were very similar in three different donors (Donors 1, 3 and 4), as shown in FIG. 4B.

The studies above indicate that optimal HIV-1 reactivation in memory T cells requires signaling events that involve, upstream, the tyrosine kinase, Lck, and, downstream, the transcription factor, NFAT.

(3) LTR Cis-Acting Elements Required for HIV-1 Reactivation.

Figure 9:
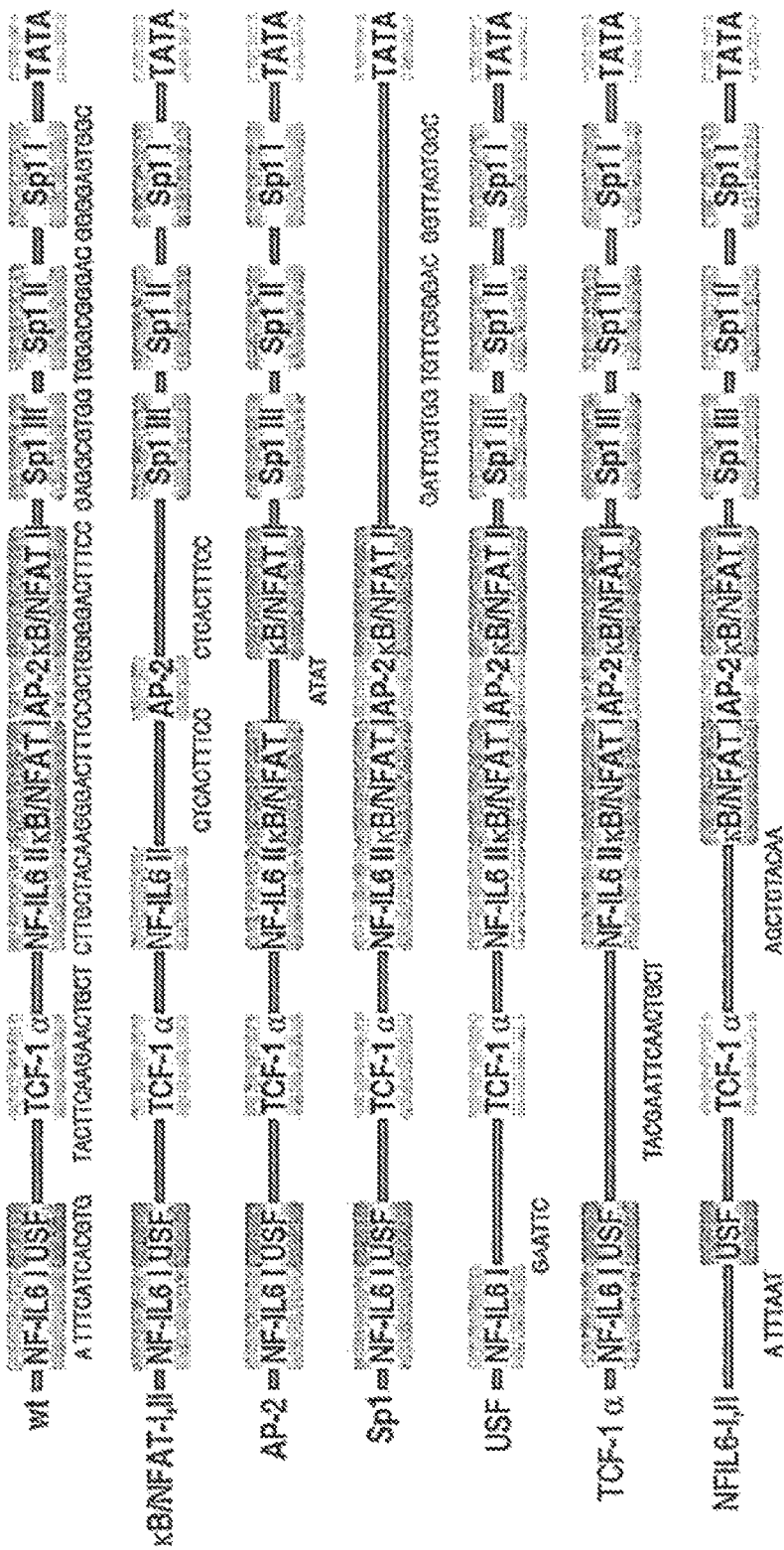
FIG. 9 shows a panel of LTR mutants. Scheme representing the different mutants generated within the HIV-1 LTR. In each one, the nucleotides mutated are represented with bold letters.

The HIV-1 latency model presented here uses molecularly cloned virus and recapitulates a single virus replication cycle. Therefore, this system allow us to ask which transcription factor binding sites in the viral promoter are required for efficient reactivation. To that end, DHIV viral construct were engineered to contain mutations in specific regions known to regulate LTR-driven transcription (Tesmer et al. 1993, Sheridan et al. 1995, Ruocco et al. 1996, Perkins et al. 1994, Jones et al. 1986, d'Adda di Fafafna et al. 1995, Bohnlein et al. 1988). These mutations were engineered in the U3 region of the 3' LTR, such that the mutant promoter was copied into the 5' end of the virus after the first round of reverse transcription. Mutants were constructed in the regions shown in FIG. 5A (See also the specific mutations in FIG. 9). NP cells were infected with mutant-promoter viruses, and cells were kept in vitro for an additional 7-day period. At this time point, immediately prior to restimulation, genomic DNA was isolated and quantitated viral integration by Alu-PCR (blue numbers in FIG. 5B), to assess the levels of latent infection prior to reactivation. The cells were then restimulated with αCD3/CD28 and analyzed intracellular p24$^{Gag}$ expression 3 days later.

Figure 5:
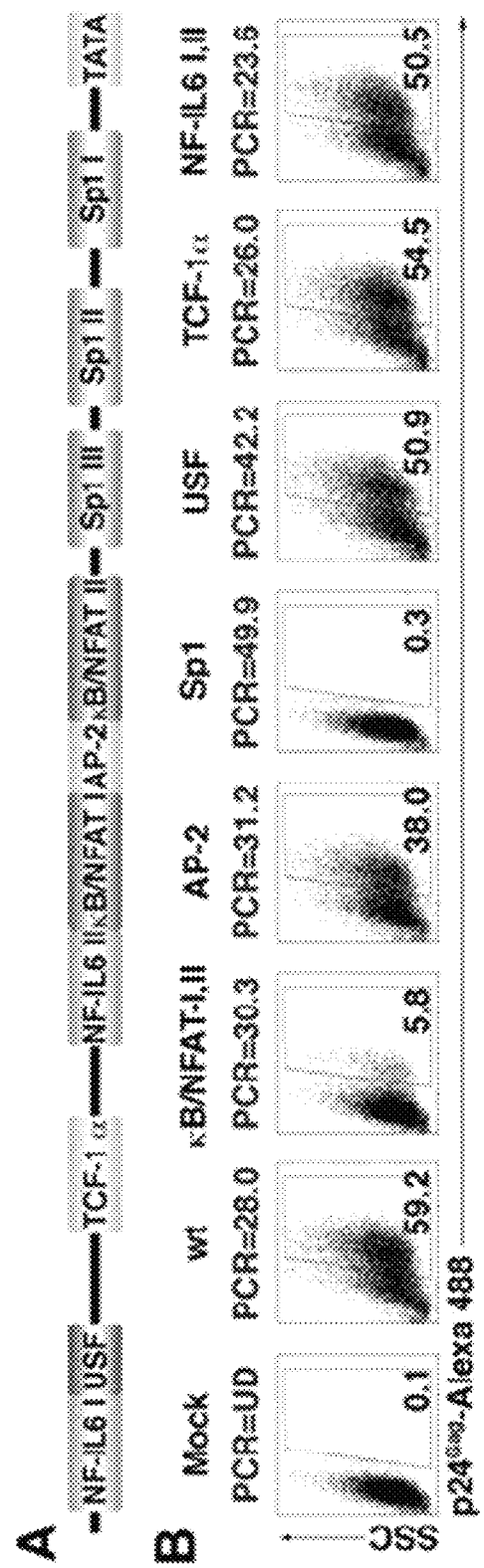
FIGS. 5A and 5B show the transcription factor binding sites involved in HIV-1 reactivation. (A) Scheme of HIV-1 LTR. (B) NP cells were infected with wt DHIV or with different LTR mutants. Mutations can be viewed in FIG. 7. 7 days after infection cells were co-stimulated with antibodies to CD3 and CD28 for 3 days and assessed for intracellular p24 gag expression by flow cytometry. The percentage of p24-postive cells is indicated in each panel. Percentage of viral integration by Alu-PCR for each virus is indicated in blue (UD=undetectable). The experiment is representative of 3 different experiments with 3 different donors.

As shown in FIG. 5B, mutation in the Sp1 sites abolished any ability of latent viruses to be reactivated (0.3%; efficiency of reactivation=([p24% of mutant with αCD3/CD28−p24% of mutant without αCD3/CD28]/[p24% of wt-virus with αCD3/CD28−p24% of wt-virus without αCD3/CD28]×100). Likewise, mutation of both κB/NFAT sites almost completely abolished reactivation (9.5%). Mutation of the AP-2 binding site led to a reactivation efficiency of 64%. Mutation of both NF-IL6 I and NF-IL6 II binding sites, USF or TCF-1α had almost no effect (equal or higher than 85% reactivation efficiency).

The viral mutagenesis results together with the inhibitor and agonist studies indicate that the transcription factors, NFAT and Sp1 are essential for reactivation in human NP memory CD4 T cells. Further dissection of signaling pathways and requirements for latency and reactivation can easily be pursued in the future using this ex vivo system.

c) Discussion

HIV-1 latency reservoirs are small, but extremely long-lived. Latent infection is associated with low-to-null levels of viral gene expression and appears to be non-cytopathic. However, upon reactivation, latent viruses enter an active mode of replication in which they are fully competent for spread and induction of disease. The current thinking in the field is that the use of a hypothetical drug that re-activates latent viruses, in combination with present-day antiretroviral drugs, is the desired approach toward viral eradication. However, the scarcity of known drugs that can safely be used for viral reactivation is a limitation. An additional limitation is the poor understanding of the dynamics between establishment of latency and reactivation, and the cellular and viral factors that govern these processes. This work describes the development of a novel method that recapitulates latent and productive viral infections in the laboratory. This method is easy to perform, powerful, and, most importantly, lends itself to molecular analysis.

One key question about HIV-1 latency is what specific cell type(s) can harbor long-lived, latent proviruses. Previous work by several groups (reviewed in (Douek et al. 2003, Persaud et al. 2003)) indicates that in vivo, quiescent memory T-cells constitute the most long-lived viral reservoir, whose decay constant ranges from months to years. Memory cells, in vivo, are subdivided into various subsets whose biology can faithfully be recapitulated in vitro (Messi et al. 2003). The relative abilities of NP, Th1 and Th2 cells to harbor latent viruses were tested and it was found that, while latent infections were induced in all subsets, NP were consistently more permissive for latent infection and accordingly less able to sustain productive infection. Conversely, Th1 cells were exquisitely sensitive to productive infection, and latent infection of these cells was significantly lower. It is tempting to speculate that the higher permissiveness to productive infection of Th1 cells was the cause of enhanced levels of apoptosis.

A unique aspect of the method presented here is that the virus is defective in Env. When the virus is produced, Env is provided in trans. Thus, upon infection, viral particles contain the full protein complement of HIV-1, and are fully infectious and competent for entry, reverse transcription, integration, and viral gene expression. However, the engineered defect in Env precludes the production of infectious progeny. Cells undergoing productive infection die within 3-5 days due to virus-mediated apoptosis and only uninfected and latently infected cells survive after the first week in culture.

A second unique feature of this system is the intrinsic ability of the virus to drive wild-type levels of gene expression. This is a crucial aspect of the model, as latent viruses in vivo, when reactivated, are fully capable of replicating and causing disease. This is an important distinction with previous models of latency in which lack of viral gene expression was associated with mutations in the virus or in the host cell (Duh et al. 1989, Kim et al. 2006, Chen et al. 1994, Cannon et al. 1994, Butera et al. 1994) or with specific sites of virus integration in heterochromatin (Jordan et al. 2003).

HIV-1 latency appears to be related to intrinsic activation and/or developmental characteristics of CD4+ T cells, rather than to the presence of latency-promoting genes in the virus. Thus, it is important to dissect, at a molecular level, the T-cell signaling pathway(s) that underlie the establishment, maintenance, and reactivation of latent infections. In the present work, a three-prong approach is used to dissect signaling events leading to reactivation in primary memory cells. Agonists and antagonists of cellular processes, and mutagenesis of viral cis-acting elements were used. The Sp1 and KB/NFAT promoter elements were critical toward reactivation.

Although Sp1 has been considered a ubiquitous and constitutive transcription factor, an emerging body of evidence indicates that the activity of Sp1 is regulated through the cell cycle (Vicart et al. 2006, Lacroix et al. 2002). Sp1 is phosphorylated and inactive in quiescent cells. Upon entry into the cell division cycle, PP2A dephosphorylates Sp1, which becomes active and tightly associated with the chromatin (Vicart et al. 2006, Lacroix et al. 2002). The finding that Sp1 is absolutely required for reactivation of latent HIV-1 is in agreement with the idea that a latently infected cell in vivo can be quiescent, and reactivation of the virus is concomitant with entry into the cell cycle.

The κB/NFAT binding sites, also a stringent requirement for viral reactivation, are not separable by mutagenesis because NFκB and NFAT bind identical elements on the LTR (Giffin et al. 2003). The potential roles played by NFAT and NFκB in reactivation are of paramount importance in these studies, as it has recently been shown that naïve cells contain very low levels of NFATc1 and NFATc2, whereas memory cells contain high levels of such transcription factors (Dienz et al. 2007). This explains why both naïve and memory T cells rapidly induce IL-2 (whose promoter contains a κB/NFAT binding site) transcription upon T cell receptor ligation, but the responsible transcription factors differ, being NFκB for naïve cells, and NFAT for memory cells (Dienz et al. 2007). Therefore, in memory cells NFAT, but not NFκB, is essential for viral reactivation. The results from the inhibitor studies clearly confirm this prediction, as CsA incubation completely blocked reactivation whereas IKK Inh or PKC inhibitors had no effect. In further support for the lack of a role of NFκB in viral reactivation in memory cells, agonists or stimuli that function through NFκB, such as PMA, prostratin and TNF-α, failed to induce any degree of reactivation.

Two agonists of NFAT activation, PHA and Ionomycin were tested. It is intriguing that PHA induced reactivation almost as efficiently as αCD3/CD28 treatment, while Ionomycin produced no detectable reactivation. PHA is a promiscuous mitogen that activates multiple pathways. However the observation that addition of CsA or PP2 completely blocked reactivation by PHA further supports that the required signaling axis downstream of PHA is Lck-Calcineurin-NFAT.

Inhibition of p38 with SB202190 had a significant effect (66% inhibition) on viral reactivation. p38 participates in two signaling events that can be relevant to viral reactivation (FIG. 8). The classical p38 activation pathway requires signaling through DAG-RasGRP/PKC-Ras, whose inhibition did not affect reactivation. In recent years, an alternative p38 activation pathway has been described, which utilizes a scaffold protein known as Dlgh1 (Round et al. 2007). Dlgh1 is devoid of any known enzymatic activity, but can modify the signaling emerging from TCR engagement, transmitted through ZAP70 and Lck, to facilitate p38 activation and subsequent activation of NFAT in a calcineurin-dependent manner (see FIG. 8). Likely, this alternative pathway (Round et al. 2007) is the target of p38 inhibition on viral reactivation.

The results are similar, although with important differences, to those reported earlier using a SCID-hu mouse model of HIV-1 latency (Brooks et al. 2003). The model by Brooks et al. and these results agree on the requirements for Lck and NFAT toward viral reactivation but disagree on the requirement of NFκB (Brooks et al. 2003). A key difference in the model proposed by Brooks et al. is the use of CD4 single-positive thymocytes, which can bare characteristics of naïve T cells rather than memory T cells.

In a Jurkat model of post-integration latency, it was found that latently infected cells frequently contained HIV-1 integrated in the proximity of alphoid repeat elements in heterochromatin (Jordan et al. 2003). Reactivation of these latent viruses was accomplished with PMA or TNF-α. PMA and TNF-α failed to induce any detectable reactivation in the latency system. The differences between these studies and the studies of Jordan et al. (Jordan et al. 2003). can be attributed to the use of a Jurkat cell line. It is well known that Jurkat and primary T cells shared some but not all T cell signaling pathways (Abraham et al. 2004). Since integration in this system is likely polyclonal, analysis of the characteristics of integration sites requires careful analysis.

Other means of inducing reactivation of latent proviruses have been proposed, based on pharmacological modification of the "histone code" with histone deacetylase inhibitors, such as valproic acid (Lehrman et al. 2005). Valproic acid was incapable of inducing viral reactivation in this model.

2. Example 2: Induction of HIV-1 Latency and Reactivation of Primary Memory CD4+ T-Cells a) Concentration of Each Inhibitor or Activator The concentration of each inhibitor or activator was as follows: 5 μM H-89, 50 μM PD98059, 250 nM Wortmannin, 15 nM bisindolylmaleimide II (BIM), 5 μM Rottlerin, 10 μM PP2, 50 μg/ml I kappa B Kinase Inhibitor Peptide, Cell-Permeable (IKK inh.) and 50 μM Forskolin (Calbiochem, San Diego, Calif.); 50 μM SB202190 and 125 ng/ml Leflunomide (Alexis Biochemicals, San Diego, Calif.); 10 nM Gö6976 and 1 μM Prostratin (LC Laboratories, Woburn, Mass.); 25 ng/ml TNF-α (Prepotech Inc.); 10 ng/ml phorbol 12-myristate 13-acetate, 1 μM Ionomycin, 5 μg/ml L-PHA and 1 mM Valproic Acid (Sigma, Saint Louis, Mo.); 500 ng/ml Cyclosporin A (Fluka/Sigma); 25 μM SP600125 (A.G. Scientific Int., San Diego, Calif.); and 20 μM Integrase Inhibitor (118-D-24).

b) Direct Mutagenesis of HIV-1 LTR

List of primers used to generate the different mutants. Nucleotides mutated are indicated in bold

```
κB/NFAT-1
Forward
                                         (SEQ ID NO: 1)
5'-tgacatcgagcttgctacaactcactttccgctggggac-3'

Reverse
                                         (SEQ ID NO: 2)
5'-gtccccagcggaaagtgagttgtagcaagctcgatgtc-3'

κB/NFAT-2
Forward
                                         (SEQ ID NO: 3)
5'-aagggactttccgctgctcactttccagggaggcg-3'

Reverse
                                         (SEQ ID NO: 4)
5'-cgcctccctggaaagtgagcggaaagtccctt-3'

AP-2
Forward
                                         (SEQ ID NO: 5)
5'-cttgctacaagggactttccatatgggacttTccagggaggcgt-3'

Reverse
                                         (SEQ ID NO: 6)
5'-cgcctccctggaaagtcccatatggaaagtcccttgtagcaag-3'

Sp-1
Forward
                                         (SEQ ID NO: 7)
5'-ggggactttccagggattcgtggcctgttcgggactggttagtggcg
ag-3'

Reverse
                                         (SEQ ID NO: 8)
5'-ctcgccactaaccagtcccgaacaggccacgaatccctggaaagtcc
cc-3'

USF
Forward
                                         (SEQ ID NO: 9)
5'-gtttgacagccgcctagcatttcatgaattcgcccgagagctgc-3'

Reverse
                                         (SEQ ID NO: 10)
5'-gcagctctcgggcgaattcatgaaatgctaggcggctgtcaaac-3'

TCF-1α
Forward
                                         (SEQ ID NO: 11)
5'-gctgcatccggagtacgaattcaactgctgacatcgagc-3'
```

-continued

Reverse
(SEQ ID NO: 12)
5'-gctcgatgtcagcagttgaattcgtactccggatgcagc-3'

NFIL6-I
Forward
(SEQ ID NO: 13)
5'-ttgacagccgcctagcatttaatcacgtggcc-3'

Reverse
(SEQ ID NO: 14)
5'-ggccacgtgattaaatgctaggcggctgtcaa-3'

NFIL6-II
Forward
(SEQ ID NO: 15)
5'-cttcaagaactgctgacatcgagagctgtacaagggactttccgctgg gga-3'

Reverse
(SEQ ID NO: 16)
5'-tccccagcggaaagtcccttgtacagctctcgatgtcagcagttcttg aag-3'

3. Example 3 a) The Effect of Homeostatic Proliferation on the Latent Reservoir.

Homeostatic proliferation is the ability of the immune system to maintain normal T-cell counts, and to correct for deviations due to expansion or depletion. Homeostatic proliferation is governed by extrinsic cellular signals, typically cytokines, in the absence of antigenic stimulation. For CD4+ memory T cells, the γc-cytokine IL-7 is key in governing this homeostasis. A role for IL-15, another γc-cytokine, has also been proposed. Homeostatic control involves both the survival and the proliferation of memory CD4+ T cells. Therefore, quiescent memory cells harboring latent proviruses can enter the cell division cycle. Reentry into the division cycle by quiescent memory cells can lead to concomitant viral reactivation. It is understood that cell division can occur in the absence of viral reactivation. Thus, homeostatic proliferation can, actually, contribute to the expansion of the latent virus reservoir over time.

b) Latently Infected Memory Cells can Divide without Reactivating Virus.

Latently infected cells where stimulated with PMA+Ionomycin. This treatment induced vigorous cellular proliferation, as well as induction of the activation markers, CD69 and CD25, but only induced a very small amount of viral reactivation (4.2% of that obtained with αCD3/αCD28). This experiment can be repeated using physiological stimuli: cytokines. In addition, the experiments can be performed under conditions that allow the skilled artisan to discern entry into the cell cycle and viral gene expression on a single-cell basis, using flow cytometry.

Figure 10:
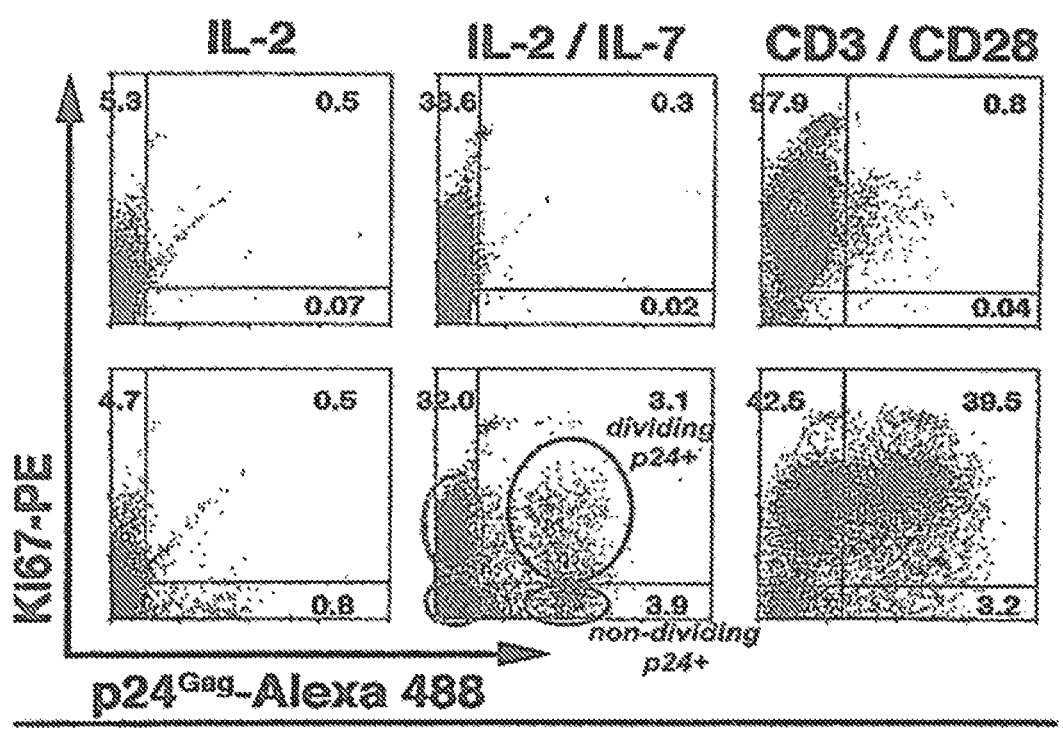
FIG. 10 shows that stimulation by IL-2+IL-7 induces viral reactivation in both dividing and non-dividing cells.

To perform these experiments, a latently infected population of cells were generated and then the cells were reactivated in the presence of IL-7 (plus IL-2, which is always maintained in culture to promote survival of cells). 48 or 72 hours later, cells were fixed, permeabilized and co-stained with two antibodies that recognize intracellular p24 (for viral reactivation) and Ki-67. Ki-67 is a nuclear antigen whose expression is tightly regulated such that it is expressed in proliferating cells but absent in resting cells. As shown in FIG. 10, stimulation with IL-2+IL-7 induced 3.1+3.9=7.0% reactivation. The distribution of these cells into Ki-67-positive (dividing; 3.1%) and negative (non-dividing; 3.9%) is similar (these populations are circled). Therefore, remarkably, 56% of the cells that showed viral reactivation by IL-7 remained in a non-dividing status. This is the second stimulus found that can uncouple cell division and viral reactivation.

As a control for maximal reactivation αCD3/αCD28 was used. As expected, this treatment induced vigorous proliferation of most cells in culture (42.5%+39.5%=82%) and most or all the p24-positive cells fell within the Ki-67-positive subset. Because αCD3/αCD28 (and its physiological counterpart, TCR engagement) induced both potent activation and proliferation, this stimulus was not adequate to address how cell division influences viral reactivation. Finally, because CD3/CD28 reactivated 39.5+3.2=42.7% of the cells while IL2+IL7 only reactivated 3.1+3.9=7.0%, there must be about 42.7-7.0=35.7% of cells still harboring latent proviruses in the IL2+IL7 stimulated cultures.

c) The Ability of Latently Infected Memory Cells to Divide without Triggering Viral Reactivation These cells are present in the subset marked with a circle in FIG. 10. The cells from this subset can be sorted and then reactivate with αCD3/αCD28, to determine the presence of latent proviruses after cells entered the cell cycle. Unfortunately, Ki-67 and p24 stainings require cell fixation, which kills the cells. Therefore, to perform this experiment viable markers can be used. Instead of p24, a virus that expresses the DsRed fluorescent protein in place of nef is used. It is understood and contemplated herein that fluorescent markers are compatible with the latency and reactivation system. After construction of DHIV-DsRed, latently infected NP cells as are generated in the manner done with DHIV-GFP. Cells are cultured in IL-2, and one week post-infection, cells are changed to medium with IL-2+IL-7. Prior to IL-7 stimulation, cells are pulsed with CFSE, and at 72 hours post stimulation, cells are subjected to flow cytometric sorting, based on green and red fluorescence. Cells that have divided have their green fluorescence (CFSE) diminished by at least half Cells that contain reactivated proviruses are red. The population that is low in CFSE and negative for DsRed is purified. The high CFSE (non-dividing) and DsRed negative cells are also purified. These populations are assayed for integrated viruses by Alu-PCR, and are cultured in IL-2 (negative control) or with αCD3/αCD28 beads, to induce maximal reactivation. 48 hours later, cells are analyzed by flow cytometry, for DsRed expression. The presence of DsRed positive cells in the αCD3/αCD28-treatment indicates that latent proviruses are indeed present in the dividing population, and indicate with what frequency. This indicates that, at least in a certain subset of IL-7-treated cells, cell division is induced without concomitant viral reactivation.

The converse scenario is that no DsRed positive cells are detected in the dividing cells in the above experiment (again, this is the equivalent of the population in FIG. 10, except done with CFSE instead of Ki-67).

d) Elucidating the Signaling Pathway that Mediates Viral Reactivation by IL-7.

Interestingly, the signaling pathway initiated by IL-7+IL-2 is independent of NFAT, because reactivation with IL-7+IL-2 is not blocked by cyclosporine A. The IL-7/IL-2 signaling pathway therefore represents an alternative means toward viral reactivation. Understanding the intracellular mediators of IL-7/IL-2 stimulation provides additional targets toward latent virus purging. Some of these mediators can be enzymes, such as kinases and phosphatases, which may be amenable to agonistic or antagonistic drugs. It is also important to know the IL-7/IL-2 signaling because, as noted herein, this pathway is the basis for homeostatic proliferation of memory cells, where an important proportion of proliferating cells are not inducing viral reactivation.

Figure 11:
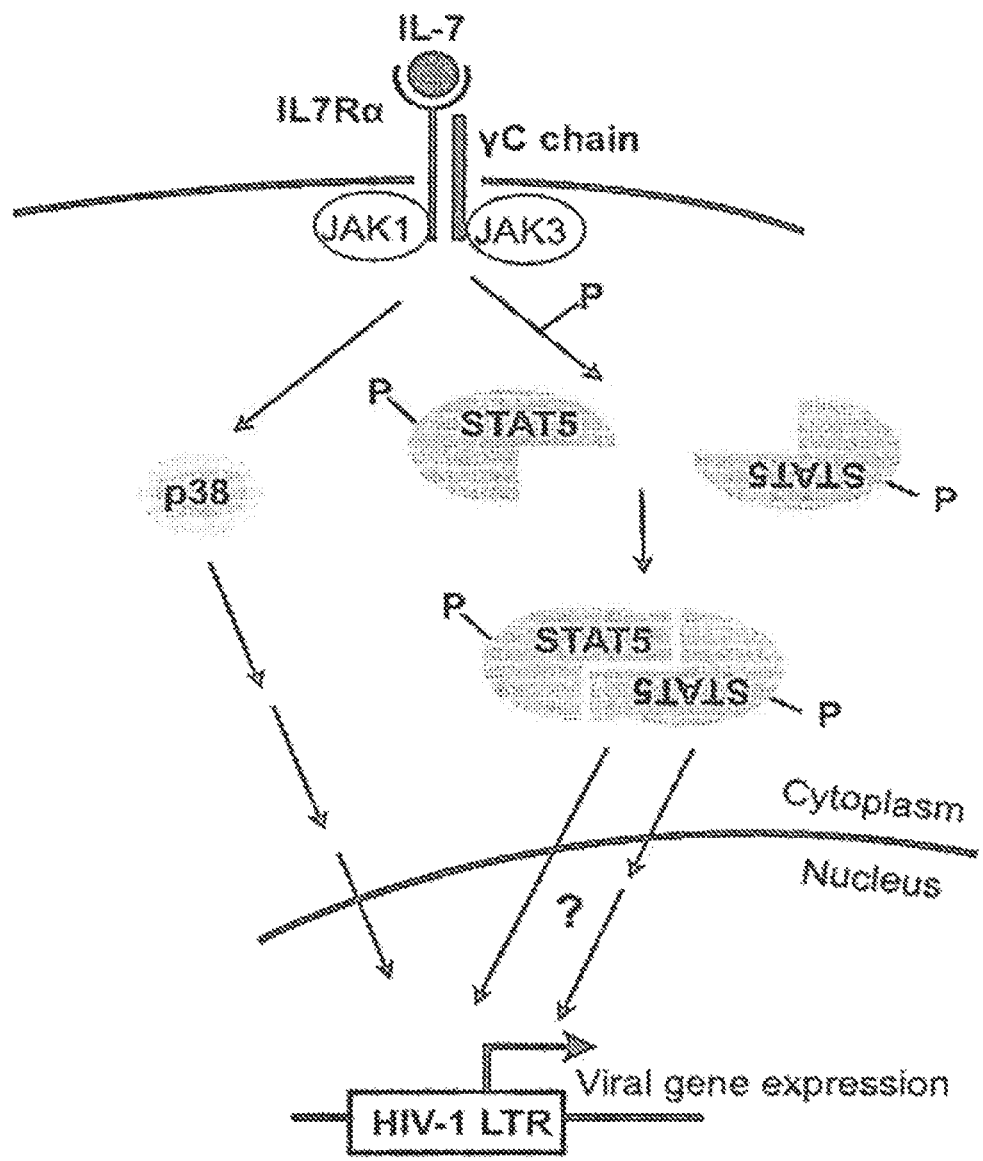
FIG. 11 shows that stimulation by IL-7 can lead to viral reactivation by two separate signaling pathways.

The canonical IL-7 pathway is illustrated in FIG. 11. This pathway uses JAK3 and JAK1 proximally, and STAT5 distally. STAT5 binding sites are present within the LTR. A recent report suggests that three consensus STAT5 binding sites can be found in the LTR. It was also shown that ectopic expression of STAT5 induced a 200-fold increase in LTR activity in cell lines, but only a 2-3 fold increase in primary cells. To ascertain the role of STAT5 in inducing LTR activity and viral reactivation, mutants in the three consensus STAT5 binding sites are constructed. Individual site mutants are constructed as well as a double Site1-and-Site2 mutant and a triple mutant. Site 3 overlaps with the KB/NFAT binding site #2. Infection with these mutants is normal, as it was for Sp1 binding site mutant. The efficiency of reactivation with IL2+IL-7 reveals the requirement of STAT5 sites for reactivation. As a control, an αCD3/αCD28 stimulation is used which is not expected to require STAT5. Further investigation of this signaling pathway includes EMSA, using synthetic oligonucleotides containing the predicted STAT5 sites, and ChIP. ChIP is performed as described herein and uses similar controls. As negative controls, STAT5 mutant viruses are used.

Figure 12:
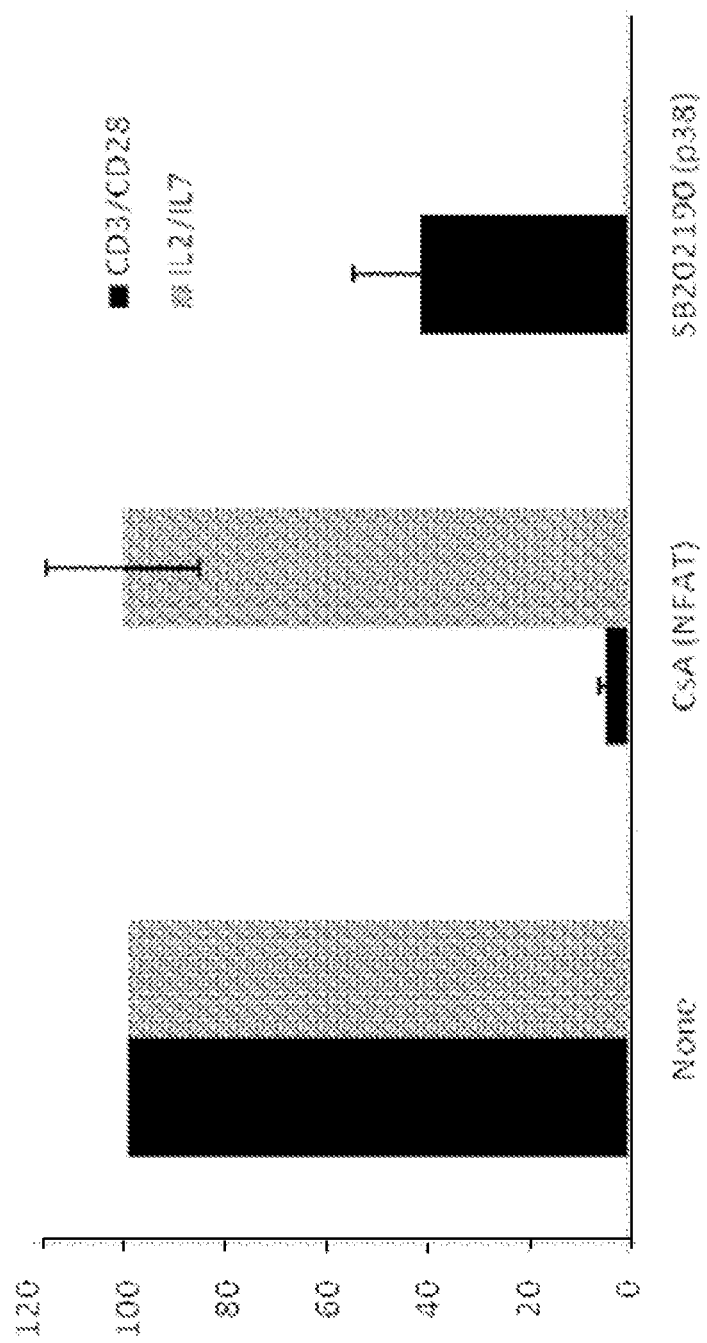
FIG. 12 shows the percentage of reactivation by either αCD3/αCD28 or IL2/IL7 stimulation following administration of an inhibitor of p38 (SB202190) or NFAT (CsA).

IL-7 stimulation induces activation of p38MAPK (a non-canonical IL-7 dependent pathway). Induction of cellular proliferation by IL-7 was reported to result in phosphorylation and activation of the p38α MAPK, and inhibition of p38α with SB203580 abrogated the proliferative response. The results show that viral reactivation after TCR engagement is partially dependent on p38 α activation (i.e., SB203580 induced about 66% inhibition). Therefore, p38α is also a mediator for reactivation via IL-7. Adding SB203580 simultaneously with IL-7 to latently infected cells can block reactivation (FIG. 12).

However, lefluonomide, a Jak3 inhibitor, does not block reactivation in memory cells and, therefore, contradicts the notion that IL-7 signaling through the canonical pathway enhances LTR activity via STAT5. On the other hand, disclosed herein is evidence that p38α, when activated downstream of αCD3/αCD28 stimulation, is required for viral reactivation. Thus, p38 is required for IL-7 reactivation. This is an exciting prospect because it means that p38α is a common signaling element required for viral reactivation through two essentially different pathways, one being NFAT-dependent (αCD3/αCD28) and the other one being independent (IL-7/IL-2). An explanation for this occurrence is the subcellular localization of two different pools of p38. One pool is cytosolic (responding to IL-7 stimulation) and the other is localized to the TCR signaling complex, in association with Dlgh1, Lck and ZAP-70. p38 activation in the latter pool is sensitive to Lck inhibition, whereas p38 in the former pool is not. Thus, the two putative pools of p38 have different targets. The phosphorylation target for p38α emanating from TCR engagement is NFAT. However, the relevant phosphorylation target for p38α, downstream of IL-7 stimulation, is not NFAT, since viral reactivation by IL-7 is insensitive to CsA.

e) Differentiation of $T_{CM}$ into $T_{EM}$ in the Absence of Antigenic Stimulation.

Central Memory T cells ($T_{CM}$) cells can differentiate into effector memory cells ($T_{EM}$) when IL-7 and IL-15 are combined with inflammatory cytokines, such as TNF-α, IL-6, IL-10 and IL-12. This differentiation provides a mechanism for replenishing effector memory cells from a pool of central memory cells, in the absence of antigenic stimulation. The ex vivo system disclosed herein can be used to investigate whether this type of differentiation is sufficient to reactivate HIV-1 from latency. Differentiation of latently infected NP cells can be induced with either IL-7 or IL-15 plus a proinflammatory cytokine (TNF-α, IL-6, IL-10 or IL-12 can be utilized separately or in combination). Differentiation of NP into $T_{EM}$ cells can be analyzed by flow cytometry.

f) Effect of Bacterial Antigens and Inflammatory Mediators on the Latent Reservoir.

The immune system is subject to multiple antigenic threats, such as bacterial antigens. The presence of bacterial antigens can in many ways induce inflammation directly or indirectly by inducing release of inflammatory cytokines by immune cells. For example, HIV-1-induced damage in the gut architecture leads to an increase in microbial translocation. This translocation leads to an increase on the levels of bacterial lipopolysaccharide (LPS) and other bacterial products in the blood stream. This increase in bacterial products in the periphery results in reactivation of latent HIV-1. Disclosed herein, the effects of different pathogen-associated molecular patterns (PAMPs), including LPS, flagellin, lipoteichoic acid, peptidoglycan, and nucleic acid variants normally associated with bacteria such as unmethylated CpG oligonucleotides are analyzed. These studies are extended to include receptors for other PAMPS, such as those recognizing double-stranded RNA (dsRNA). Since these products can act directly on PAMP recognition molecules, and induce the release of pro-inflammatory cytokines and chemokines, select pro-inflammatory cytokines and chemokines are analyzed for their ability to reactivate latent viruses.

PAMPs are mainly recognized by cells of the innate immune system, such as monocyte/macrophages and dendritic cells, through the interaction with a family of receptors called Toll-like receptors (TLRs 1-10). Specifically, TLR-4 recognizes LPS. Two different pathways are activated after TLR-4 ligation. The first one involves activation of NFκB and the production of inflammatory cytokines, such as IL-1, IL-6, TNF-α or TGF-β. The second one involves activation of IRF3, which leads to the production of IFN-β and interferon inducible genes. These cytokines can then bind to receptors on latently infected $T_{CM}$, to induce reactivation.

Monocytes are treated with TLR agonists (such as LPS, for TLR4), and test the supernatant of treated monocytes on latently infected cells. When supernatants are able to induce viral reactivation, antibodies against IL-1, IL-6, TNF-α, TGF-β and IFN-β are used to block individual cytokines and elucidate the involvement of particular cytokines.

Herein, the effects of PAMPs acting directly on latently infected cells are disclosed. A growing body of evidence indicates that TLR expression can also be detected in T cells. However, no information is available regarding the expression of these receptors on central memory CD4 T cells. The expression of TLR receptors in NP cells is analyzed by flow cytometry. The expression of these receptors are confirmed on $T_{CM}$ directly obtained from peripheral blood (instead of NP) using flow cytometry. Once identified the expression of TLRs in NP cells, similar studies of reactivation are performed on latently infected NP cells as the ones described above. TLR4 and its downstream signaling has been dealt with separately in more detail. To study the potential for reactivation, latently infected cells are incubated with specific agonists for each TLR, and reactivation are measured as % p24(+) cells.

F. REFERENCES

1. Finzi D, Hermankova M, Pierson T, et al. Identification of a reservoir for HIV-1 in patients on highly active antiretroviral therapy. Science. 1997; 278:1295-1300.
2. Chun T W, Carruth L, Finzi D, et al. Quantification of latent tissue reservoirs and total body viral load in HIV-1 infection. Nature. 1997; 387:183-188.
3. Folks T M, Clouse K A, Justement J, et al. Tumor necrosis factor alpha induces expression of human immunodeficiency virus in a chronically infected T-cell clone. Proc Natl Acad Sci USA. 1989; 86:2365-2368.
4. Antoni B A, Rabson A B, Kinter A, Bodkin M, Poli G. NF-kappa B-dependent and -independent pathways of HIV activation in a chronically infected T cell line. Virology. 1994; 202:684-694.
5. Jordan A, Bisgrove D, Verdin E. HIV reproducibly establishes a latent infection after acute infection of T cells in vitro. Embo J. 2003; 22:1868-1877.
6. Folks T M, Justement J, Kinter A, Dinarello C A, Fauci A S. Cytokine-induced expression of HIV-1 in a chronically infected promonocyte cell line. Science. 1987; 238:800-802.
7. Brooks D G, Kitchen S G, Kitchen C M, Scripture-Adams D D, Zack J A. Generation of HIV latency during thymopoiesis. Nat Med. 2001; 7:459-464.
8. Lahm H W, Stein S. Characterization of recombinant human interleukin-2 with micromethods. J Chromatogr. 1985; 326:357-361.
9. Svarovskaia E S, Barr R, Zhang X, et al. Azido-containing diketo acid derivatives inhibit human immunodeficiency virus type 1 integrase in vivo and influence the frequency of deletions at two-long-terminal-repeat-circle junctions. J Virol. 2004; 78:3210-3222.
10. Simm M, Shahabuddin M, Chao W, Allan J S, Volsky D J. Aberrant Gag protein composition of a human immunodeficiency virus type 1 vif mutant produced in primary lymphocytes. J Virol. 1995; 69:4582-4586.
11. Messi M, Giacchetto I, Nagata K, Lanzavecchia A, Natoli G, Sallusto F. Memory and flexibility of cytokine gene expression as separable properties of human T(H)1 and T(H)2 lymphocytes. Nat Immunol. 2003; 4:78-86.
12. Zhu Y, Gelbard H A, Roshal M, Pursell S, Jamieson B D, Planelles V. Comparison of cell cycle arrest, transactivation, and apoptosis induced by the simian immunodeficiency virus SIVagm and human immunodeficiency virus type 1 vpr genes. J Virol. 2001; 75:3791-3801.
13. Gomez-Benito M, Balsas P, Bosque A, Anel A, Marzo I, Naval J. Apo2L/TRAIL is an indirect mediator of apoptosis induced by interferon-alpha in human myeloma cells. FEBS Lett. 2005; 579:6217-6222.
14. Vandegraaff N, Kumar R, Hocking H, et al. Specific inhibition of human immunodeficiency virus type 1 (HIV-1) integration in cell culture: putative inhibitors of HIV-1 integrase. Antimicrob Agents Chemother. 2001; 45:2510-2516.
15. Butler S L, Hansen M S, Bushman F D. A quantitative assay for HIV DNA integration in vivo. Nat Med. 2001; 7:631-634.
16. Dehart J L, Andersen J L, Zimmerman E S, et al. The ataxia telangiectasia-mutated and Rad3-related protein is dispensable for retroviral integration. J Virol. 2005; 79:1389-1396.
17. Rivino L, Messi M, Jarrossay D, Lanzavecchia A, Sallusto F, Geginat J. Chemokine receptor expression identifies Pre-T helper (Th)1, Pre-Th2, and nonpolarized cells among human CD4+ central memory T cells. J Exp Med. 2004; 200:725-735.
18. Andersen J L, DeHart J L, Zimmerman E S, et al. HIV-1 Vpr-induced apoptosis is cell cycle dependent and requires Bax but not ANT. PLoS Pathog. 2006; 2:e127.
19. Challita-Eid P M, Klimatcheva E, Day B T, et al. Inhibition of HIV type 1 infection with a RANTES-IgG3 fusion protein. AIDS Res Hum Retroviruses. 1998; 14:1617-1624.
20. Brenchley J M, Hill B J, Ambrozak D R, et al. T-cell subsets that harbor human immunodeficiency virus (HIV) in vivo: implications for HIV pathogenesis. J Virol. 2004; 78:1160-1168.
21. Kane L P, Lin J, Weiss A. Signal transduction by the TCR for antigen. Curr Opin Immunol. 2000; 12:242-249.
22. Isakov N, Mally M I, Scholz W, Altman A. T-lymphocyte activation: the role of protein kinase C and the bifurcating inositol phospholipid signal transduction pathway. Immunol Rev. 1987; 95:89-111.
23. Bauer B, Krumbock N, Ghaffari-Tabrizi N, et al. T cell expressed PKCtheta demonstrates cell-type selective function. Eur J Immunol. 2000; 30:3645-3654.
24. Swaroop N, Chen F, Wang L, Dokka S, Toledo D, Rojanasakul Y. Inhibition of nuclear transcription factor-kappaB by specific IkappaB kinase peptide inhibitor. Pharm Res. 2001; 18:1631-1633.
25. Lin J, Weiss A. T cell receptor signalling. J Cell Sci. 2001; 114:243-244.
26. Franke T F, Yang S I, Chan T O, et al. The protein kinase encoded by the Akt proto-oncogene is a target of the PDGF-activated phosphatidylinositol 3-kinase. Cell. 1995; 81:727-736.
27. Nordheim A. Transcription factors. CREB takes CBP to tango. Nature. 1994; 370:177-178.
28. Osborn L, Kunkel S, Nabel G J. Tumor necrosis factor alpha and interleukin 1 stimulate the human immunodeficiency virus enhancer by activation of the nuclear factor kappa B. Proc Natl Acad Sci USA. 1989; 86:2336-2340.
29. Duh E J, Maury W J, Folks T M, Fauci A S, Rabson A B. Tumor necrosis factor alpha activates human immunodeficiency virus type 1 through induction of nuclear factor binding to the NF-kappa B sites in the long terminal repeat. Proc Natl Acad Sci USA. 1989; 86:5974-5978.
30. Ylisastigui L, Archin N M, Lehrman G, Bosch R J, Margolis D M. Coaxing HIV-1 from resting CD4 T cells: histone deacetylase inhibition allows latent viral expression. Aids. 2004; 18:1101-1108.
31. Simon G, Moog C, Obert G. Valproic acid reduces the intracellular level of glutathione and stimulates human immunodeficiency virus. Chem Biol Interact. 1994; 91:111-121.
32. Lehrman G, Hogue I B, Palmer S, et al. Depletion of latent HIV-1 infection in vivo: a proof-of-concept study. Lancet. 2005; 366:549-555.
33. Tesmer V M, Rajadhyaksha A, Babin J, Bina M. NF-IL6-mediated transcriptional activation of the long terminal repeat of the human immunodeficiency virus type 1. Proc Natl Acad Sci USA. 1993; 90:7298-7302.
34. Sheridan P L, Sheline C T, Cannon K, et al. Activation of the HIV-1 enhancer by the LEF-1 HMG protein on nucleosome-assembled DNA in vitro. Genes Dev. 1995; 9:2090-2104.
35. Ruocco M R, Chen X, Ambrosino C, et al. Regulation of HIV-1 long terminal repeats by interaction of C/EBP(NF-IL6) and NF-kappaB/Rel transcription factors. J Biol Chem. 1996; 271:22479-22486.

36. Perkins N D, Agranoff A B, Duckett C S, Nabel G J. Transcription factor AP-2 regulates human immunodeficiency virus type 1 gene expression. J Virol. 1994; 68:6820-6823.
37. Jones K A, Kadonaga J T, Luciw P A, Tjian R. Activation of the AIDS retrovirus promoter by the cellular transcription factor, Sp1. Science. 1986; 232:755-759.
38. d'Adda di Fagagna F, Marzio G, Gutierrez M I, Kang L Y, Falaschi A, Giacca M. Molecular and functional interactions of transcription factor USF with the long terminal repeat of human immunodeficiency virus type 1. J Virol. 1995; 69:2765-2775.
39. Bohnlein E, Lowenthal J W, Siekevitz M, Ballard D W, Franza B R, Greene W C. The same inducible nuclear proteins regulates mitogen activation of both the interleukin-2 receptor-alpha gene and type 1 HIV. Cell. 1988; 53:827-836.
40. Douek D C, Picker L J, Koup R A. T cell dynamics in HIV-1 infection. Annu Rev Immunol. 2003; 21:265-304.
41. Persaud D, Zhou Y, Siliciano J M, Siliciano R F. Latency in human immunodeficiency virus type 1 infection: no easy answers. J Virol. 2003; 77:1659-1665.
42. Kim Y K, Bourgeois C F, Pearson R, et al. Recruitment of TFIIH to the HIV LTR is a rate-limiting step in the emergence of HIV from latency. Embo J. 2006; 25:3596-3604.
43. Chen B K, Saksela K, Andino R, Baltimore D. Distinct modes of human immunodeficiency virus type 1 proviral latency revealed by superinfection of nonproductively infected cell lines with recombinant luciferase-encoding viruses. J Virol. 1994; 68:654-660.
44. Cannon P, Kim S H, Ulich C, Kim S. Analysis of Tat function in human immunodeficiency virus type 1-infected low-level-expression cell lines U1 and ACH-2. J Virol. 1994; 68:1993-1997.
45. Butera S T, Roberts B D, Lam L, Hodge T, Folks T M. Human immunodeficiency virus type 1 RNA expression by four chronically infected cell lines indicates multiple mechanisms of latency. J Virol. 1994; 68:2726-2730.
46. Vicart A, Lefebvre T, Imbert J, Fernandez A, Kahn-Perles B. Increased chromatin association of Sp1 in interphase cells by PP2A-mediated dephosphorylations. J Mol Biol. 2006; 364:897-908.
47. Lacroix I, Lipcey C, Imbert J, Kahn-Perles B. Sp1 transcriptional activity is up-regulated by phosphatase 2A in dividing T lymphocytes. J Biol Chem. 2002; 277:9598-9605.
48. Giffin M J, Stroud J C, Bates D L, von Koenig K D, Hardin J, Chen L. Structure of NFAT1 bound as a dimer to the HIV-1 LTR kappa B element. Nat Struct Biol. 2003; 10:800-806.
49. Dienz O, Eaton S M, Krahl T J, et al. Accumulation of NFAT mediates IL-2 expression in memory, but not naive, CD4+ T cells. Proc Natl Acad Sci USA. 2007; 104:7175-7180.
50. Round J L, Humphries L A, Tomassian T, Mittelstadt P, Zhang M, Miceli M C. Scaffold protein Dlgh1 coordinates alternative p38 kinase activation, directing T cell receptor signals toward NFAT but not NF-kappaB transcription factors. Nat Immunol. 2007; 8:154-161.
51. Brooks D G, Hamer D H, Arlen P A, et al. Molecular characterization, reactivation, and depletion of latent HIV. Immunity. 2003; 19:413-423.
52. Abraham R T, Weiss A. Jurkat T cells and development of the T-cell receptor signalling paradigm. Nat Rev Immunol. 2004; 4:301-308.

What is claimed is:

1. A method of screening for a composition that activates a cell latently infected by a virus; the method comprising the steps of:
   a) creating a latently infected cell using the method of comprising the steps of: a) isolating uninfected primary CD4+,CD27+, CD45RO— naïve T cells; b) priming the CD4+,CD27+, CD45RO— naive T cells toward differentiation, wherein at least a portion of the primary CD4+,CD27+, CD45RO— naïve T cells differentiate into non-polarized CD4+, CD27+, CD45RO+memory T cells; c) exposing the non-polarized cells of step b) to a lentivirus defective in env, wherein the lentivirus comprises one or more sequences of interest operatively inserted downstream of a lentiviral promoter, wherein the one or more sequences of interest are HIV genes that encode one or more HIV proteins, wherein the one or more HIV proteins comprise at least Tat and Rev, thereby creating a population of cells latently infected with the lentivirus; and d) stimulating the latently infected cells to reactivate the latent virus, wherein stimulating results in the expression of at least Tat and Rev;
   e) exposing the cell to a test composition; and
   f) determining if the latently infected cell becomes active.

2. The method of claim 1, wherein the cell is exposed to CD3/CD28 antibodies during step b).

3. The method of claim 1, wherein the cell is exposed to PHA during step b).

4. The method of claim 1, wherein the virus is a retrovirus.

5. The method of claim 4, wherein the retrovirus is selected from the group comprising HIV-1, HIV-2, or SIV.

6. The method of claim 1, wherein at least 10% the population of cells is latently infected.

7. The method of claim 1, wherein at least 20% of the population of cells is latently infected.

8. The method of claim 1, wherein at least 30% of the population of cells is latently infected.

9. The method of claim 1, wherein at least 40% of the population of cells is latently infected.

10. The method of claim 1, wherein the lentiviral promoter is a HIV or SIV promoter.

11. The method of claim 1, wherein the Env is provided intrans to the Env Defective lentivirus while the lentivirus is being grown, prior to exposure to the non-polarized cells of step c).

12. The method of claim 1, wherein the lentivirus does not contain a transgene.

13. The method of claim 1, wherein the lentivirus defective in Env is a defective HIV (DHIV) vector.

14. The method of claim 1, wherein the population of cells latently infected with the lentivirus can be activated to support transcription of the lentivirus genes of the lentivirus.

15. The method of claim 1, wherein the lentivirus further comprises HIV genes that encode Gag and Pol.

* * * * *